(12) United States Patent
Maly et al.

(10) Patent No.: US 12,685,765 B2
(45) Date of Patent: Jul. 21, 2026

(54) POLYPEPTIDES MIMICKING MPER AND V3-LOOP HIV-1 Env GLYCOPROTEIN EPITOPES

(71) Applicants: UNIVERZITA PALACKEHO V OLOMOUCI, Olomouc (CZ); NEXIUM, S.R.O., Chlumec nad Cidlinou (CZ)

(72) Inventors: Petr Maly, Prague (CZ); Milan Raska, Olomouc (CZ); Milan Kuchar, Sobulky (CZ); Petr Kosztyu, Olomouc (CZ); Jiri Cerny, Plzen (CZ); Veronika Daniel Liskova, Prague (CZ); Hana Petrokova, Prague (CZ)

(73) Assignees: UNIVERZITA PALACKEHO V OLOMOUCI, Olomouc (CZ); NEXIUM, S.R.O., Chlumec nad Cidlinou (CZ)

( * ) Notice: Subject to any disclaimer, the term of this patent is extended or adjusted under 35 U.S.C. 154(b) by 490 days.

(21) Appl. No.: 18/278,208

(22) PCT Filed: Feb. 18, 2022

(86) PCT No.: PCT/CZ2022/050017
§ 371 (c)(1),
(2) Date: Aug. 22, 2023

(87) PCT Pub. No.: WO2022/179648
PCT Pub. Date: Sep. 1, 2022

(65) Prior Publication Data

US 2024/0131147 A1    Apr. 25, 2024
US 2024/0226269 A9    Jul. 11, 2024

(30) Foreign Application Priority Data

Feb. 26, 2021   (EP) .................................... 21159446

(51) Int. Cl.
*A61K 39/21*      (2006.01)
*A61K 39/00*      (2006.01)
*A61P 31/18*      (2006.01)
*C07K 14/005*      (2006.01)

(52) U.S. Cl.
CPC .............. *A61K 39/21* (2013.01); *A61P 31/18* (2018.01); *C07K 14/005* (2013.01); *A61K 2039/575* (2013.01)

(58) Field of Classification Search
None
See application file for complete search history.

(56) References Cited

FOREIGN PATENT DOCUMENTS

WO      2015104403 A1    7/2015

OTHER PUBLICATIONS

Kosztyu, Petr, et al.; "Proteins mimicking epitope of HIV-1 virus neutralizing antibody induce virus-neutralizing sera in mice"; EBioMedicine 2019; 47:247-256.
Sok, Devin, et al.; "Recent progress in broadly neutralizing antibodies to HIV"; Nature Immunology 2018; 19(11):1179-1188.
Kuchar, Milan, et al.; "Myomedin scaffold variants targeted to 10E8 HIV-1 broadly neutralizing antibody mimic gp41 epitope and elicit HIV-1 virus-neutralizing sera in mice"; Virulence 2021; 12(1):1271-1287.
International Search Report and Written Opinion for PCT Application No. PCT/CZ2022/050017, mailed Jun. 29, 2022.
International Application Status Report generated Aug. 3, 2023.

*Primary Examiner* — Nicole Kinsey White
*Assistant Examiner* — Ruixue Wang
(74) *Attorney, Agent, or Firm* — Notaro, Michalos & Zaccaria P.C.

(57) ABSTRACT

Polypeptides having a length of up to 180 amino acids and containing a sequence selected from sequences identical or differing at most in 5 amino acids from the sequence:

KSELAVEILEKGQVRFWMQA$X_{21}X_{22}X_{23}X_{24}$GNAKVNYIFNEKEIFEG

PKYKMHID$X_{50}X_{51}X_{52}$GIIEMFMEKLQDEDEGTYTFQLQ $X_{76}X_{77}X_{78}X_{79}X_{80}$NHSTVVLVGDVFKKLQKEAEFQRQEWIRKQG.

17 Claims, 15 Drawing Sheets
Specification includes a Sequence Listing.

Fig. 1A          Fig. 1B
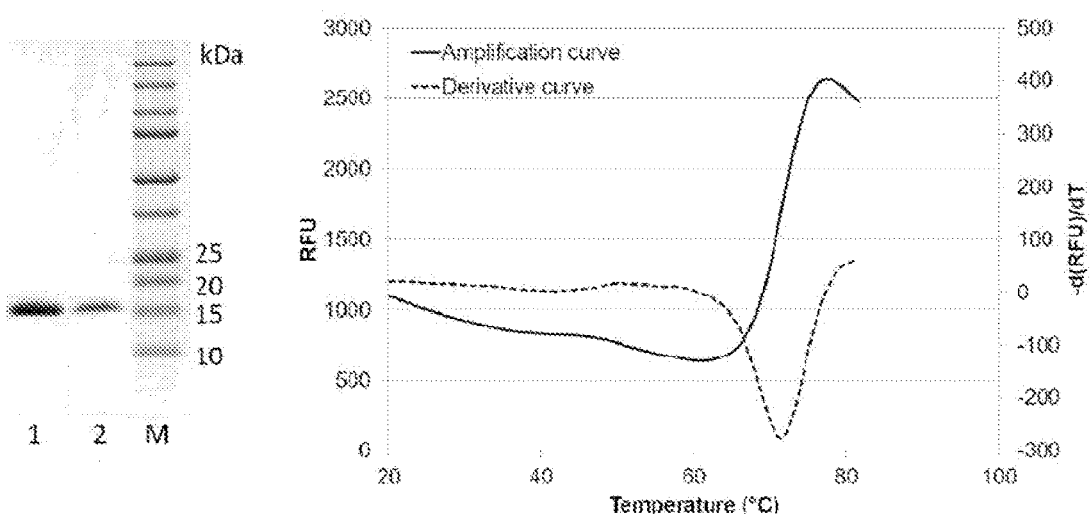
Fig. 2A          Fig. 2B
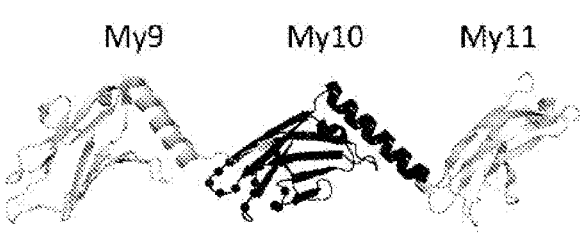

Fig. 4A
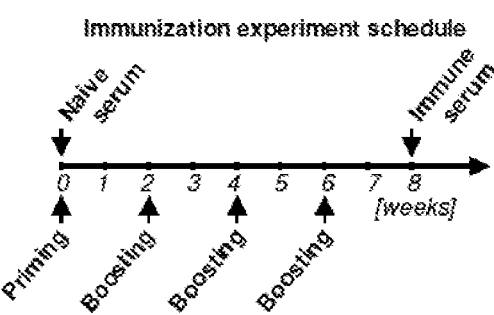
Fig. 4B
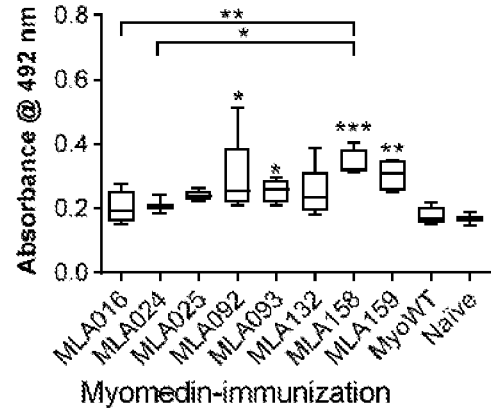
Fig. 4C
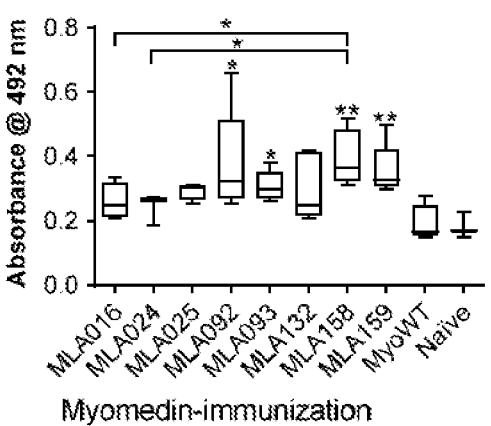
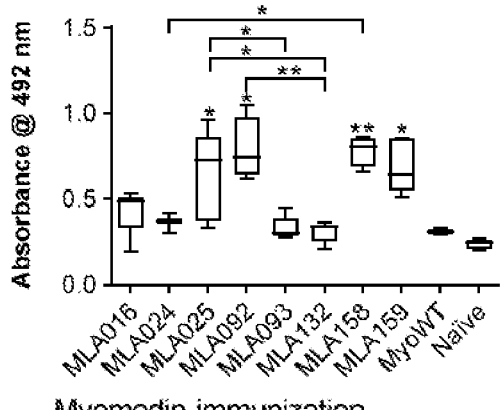
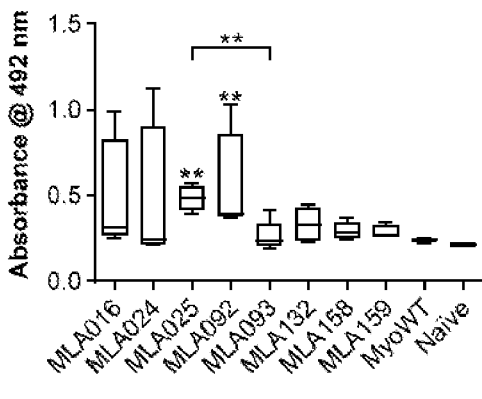

Fig. 4D, continued
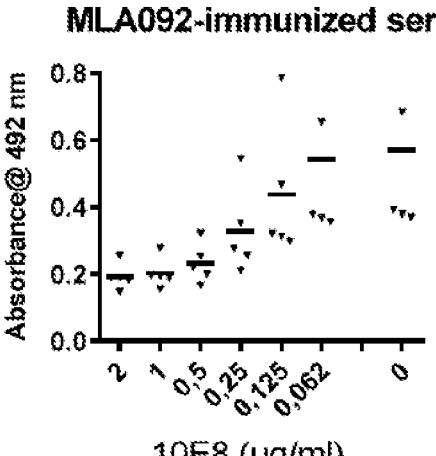
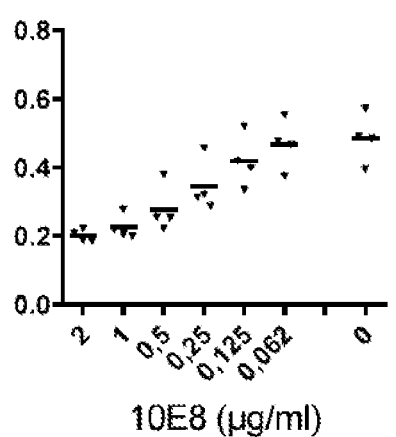
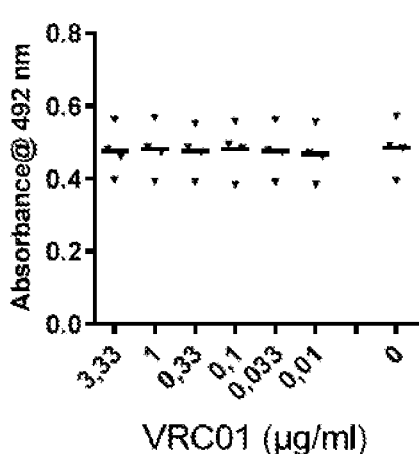
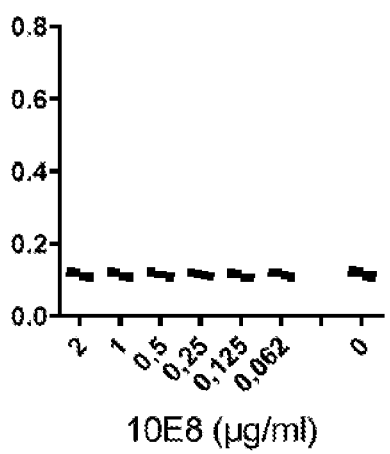
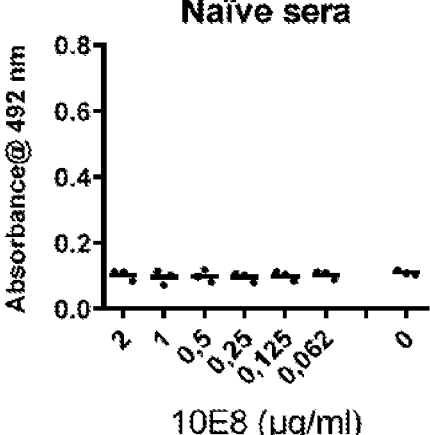

Fig. 5, continued
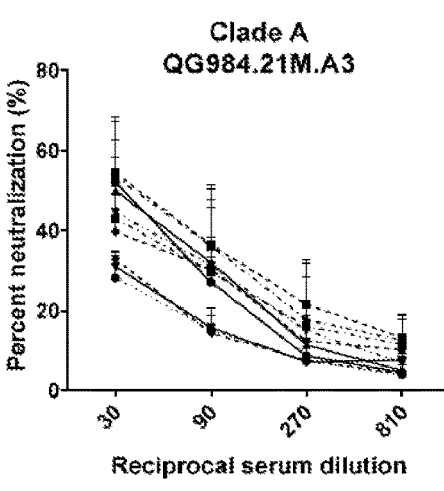
Clade A
QG984.21M.A3
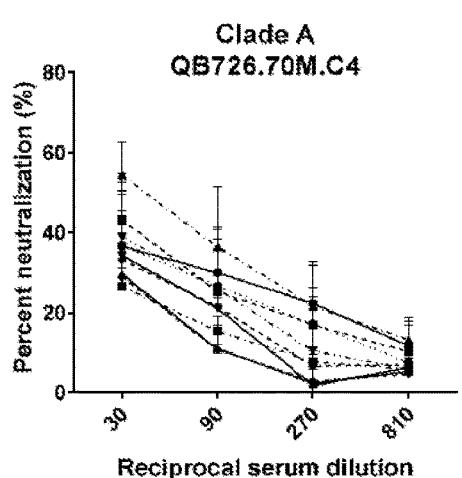
Clade A
QB726.70M.C4
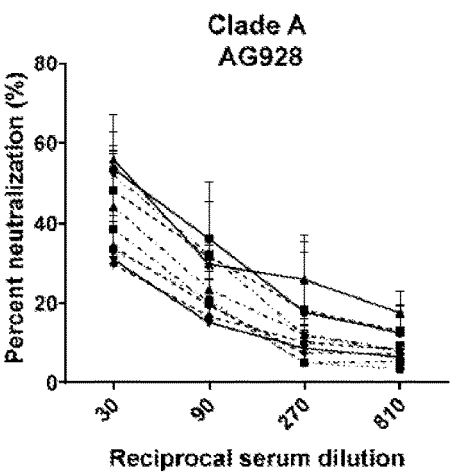
Clade A
AG928
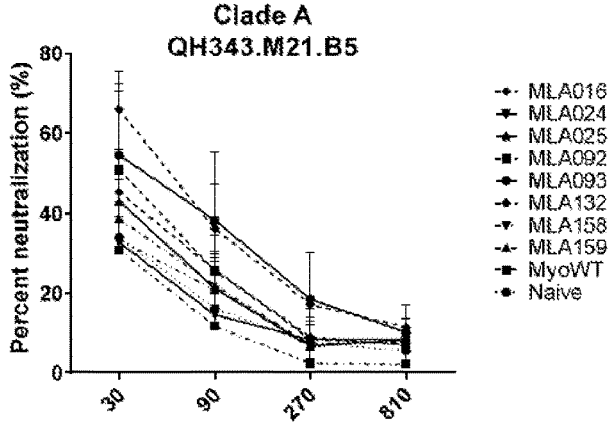
Clade A
QH343.M21.B5

Fig. 5, continued
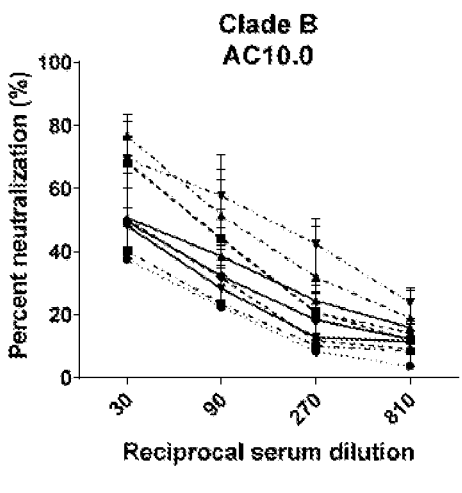
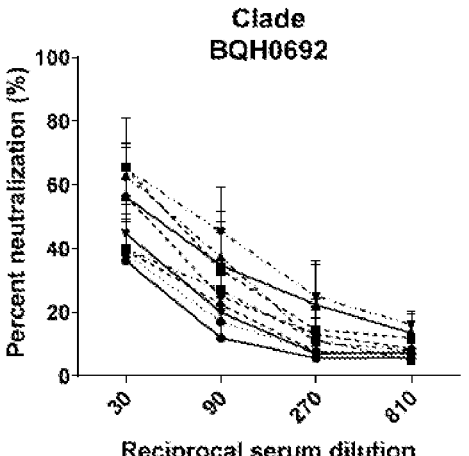
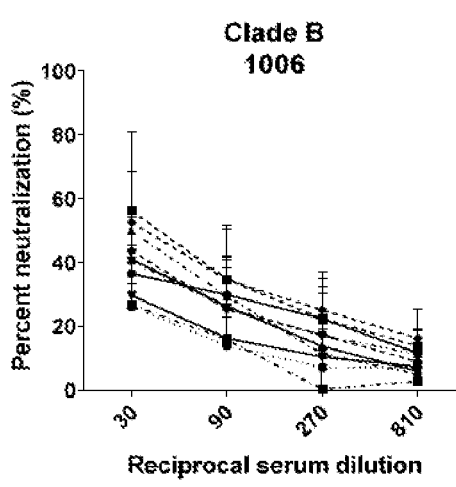
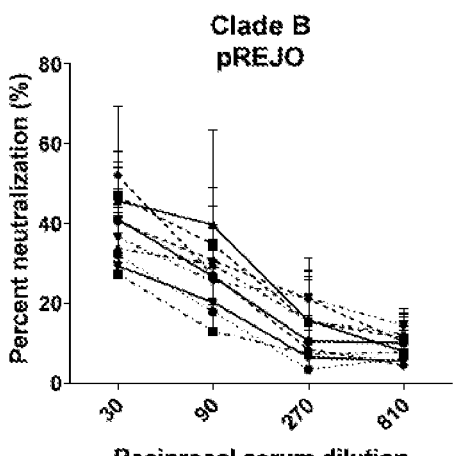
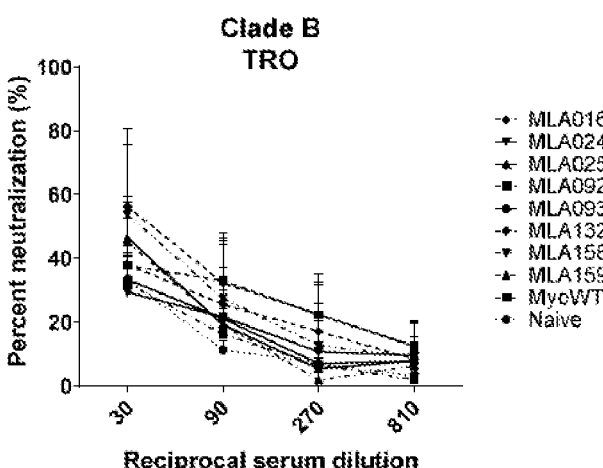

Fig. 5, continued
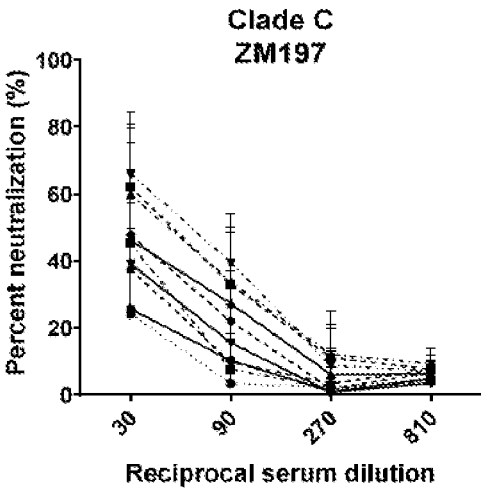
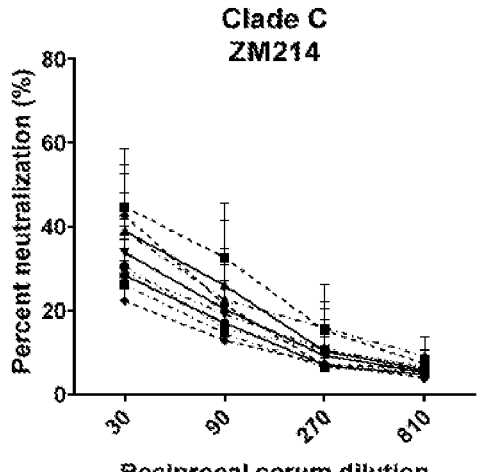
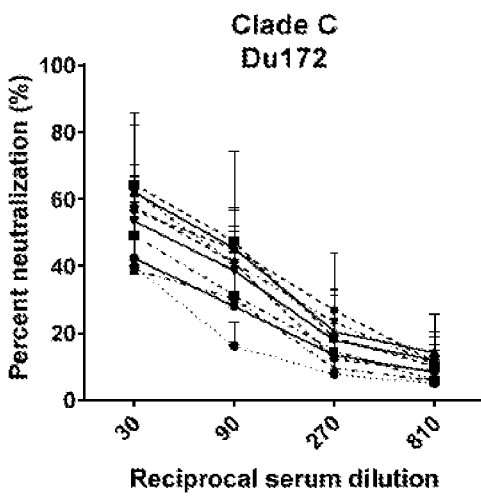
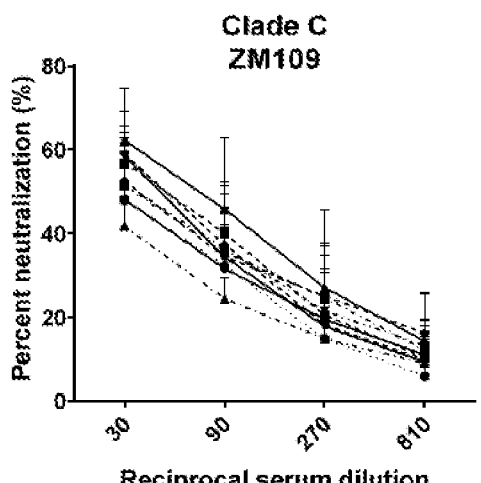
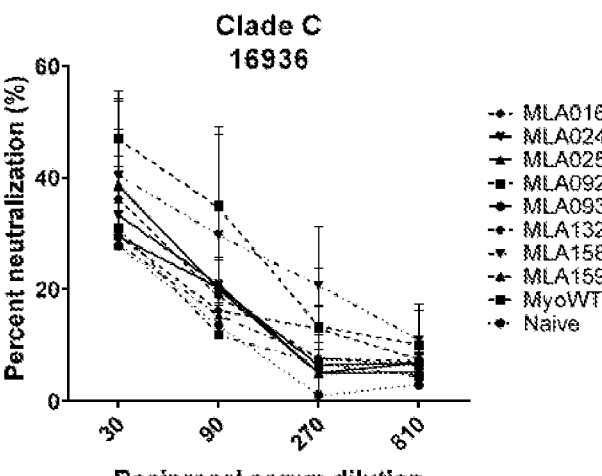

Fig. 5, continued
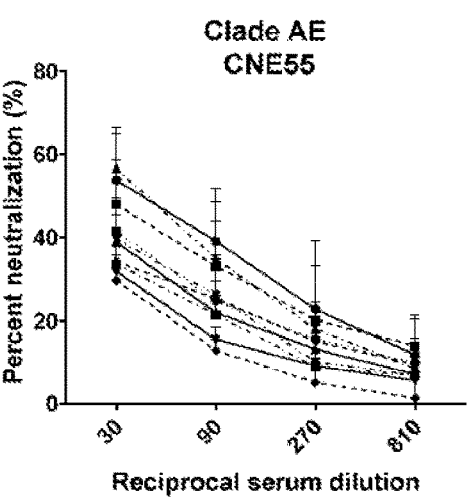
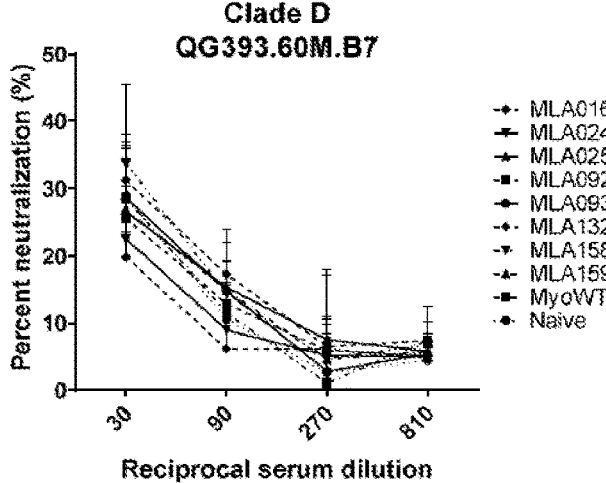

Fig. 10
Serum Env specific IgG after
3. immunization
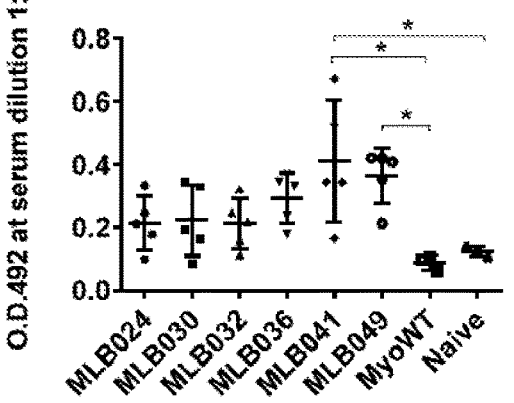
Serum Env specific IgG after
4. immunization
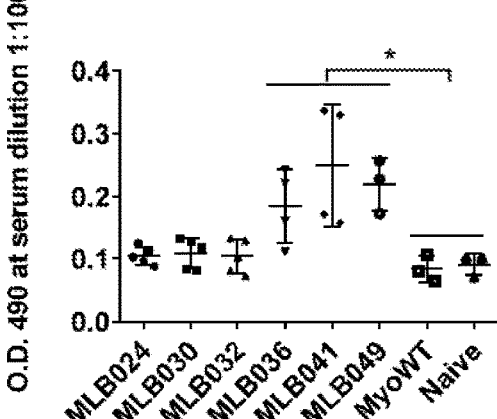

Fig. 11
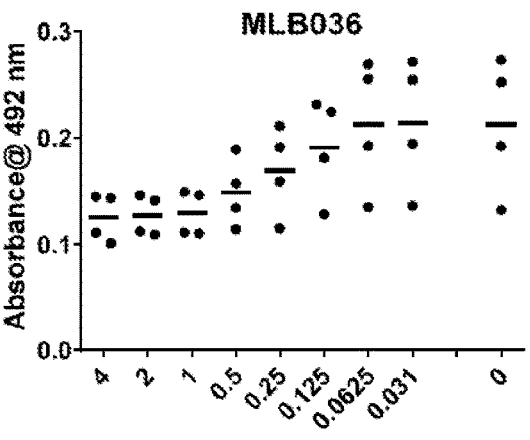
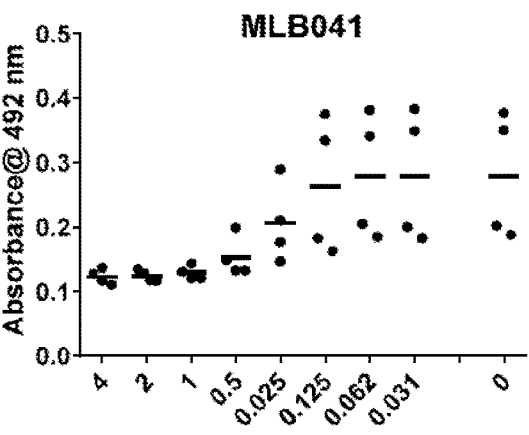
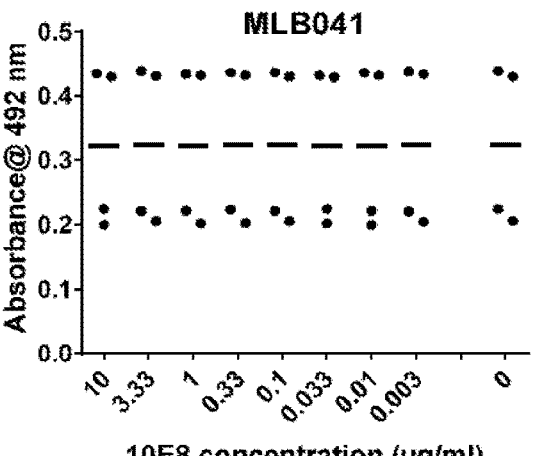
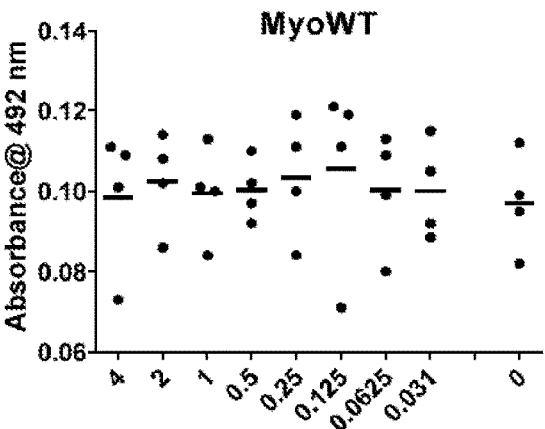

POLYPEPTIDES MIMICKING MPER AND V3-LOOP HIV-1 Env GLYCOPROTEIN EPITOPES

FIELD OF THE INVENTION

The present invention relates to polypeptides derived from the structure of human contractile protein myomesin-1 domain. The polypeptides of the present invention include three groups of polypeptides designated MLA, MLB and MLD targeted to 10E8, PGT126, and PGT121 broadly neutralizing antibodies (bNAbs) against HIV-1 virus, respectively. The polypeptides recognize a paratope of the particular HIV-1 bNAb and mimic the cognate epitopes of Env glycoprotein and are, therefore, suitable as immunogens for stimulation of production of HIV-1-neutralizing antibodies and for the development of a vaccine preventing HIV infection.

BACKGROUND ART

Stimulation of protective immunity by the production of broadly neutralizing antibodies (bNAbs) in immunized individuals remains a challenge in HIV-1 vaccine development. Identification and characterization of highly potent bNAbs cloned from B-cells of elite neutralizers provide a molecular clue for designing new vaccine strategies. The main target of neutralizing antibody on the HIV-1 virus surface is the envelope glycoprotein (Env), heterotrimer composed of three identical gp120/gp41 subunits. Gp120 protrudes from virus surface whereas gp41 is transmembrane subunit. Systematic studies of specificity, binding affinity, breadth and potency led to a clustering of bNAbs into four major groups specific for V2 loop of HIV-1 Env glycoproteins (V2 bNAbs), V3 glycan (V3 bNAbs), CD4 binding site (CD4 bNAbs) and membrane-proximal external region (MPER bNAbs) (Moore, P. L. The Neutralizing Antibody Response to the HIV-1 Env Protein. Curr HIV Res 16, 21-28, 2018). Some of these bNAbs exhibit extraordinary breadth and potency and efficiently neutralize viral infection of host cells and represent exclusive candidates for vaccine design and therapy (Sok, D., and Burton, D. R. Recent progress in broadly neutralizing antibodies to HIV. Nat Immunol 19, 1179-1188, 2018).

To overcome persisting problems with low-efficient immunization by Env/gp120 and Env-modified glycan-carrying immunogens, we recently proposed a novel strategy that is based on immunization by artificial scaffold proteins mimicking HIV-1 Env epitope (Kosztyu, P., Kuchar, M., Cerny, J., Barkociova, L., Maly, M., Petrokova, H., Czernekova, L., Liskova, V., Raskova Kafkova, L., Knotigova, P., et al., Proteins mimicking epitope of HIV-1 virus neutralizing antibody induce virus-neutralizing sera in mice. EBioMedicine 47, 247-256, 2019). These protein variants selected from a highly complex albumin-binding domain-derived combinatorial library by directed evolution can function as "protein imprints" of paratopes of the most-potent HIV-1 bNAbs. In our proof-of-concept study, we demonstrated that variants called VRA017, VRA019 and VRA177 mimicking epitope of VRC01 bNAb elicited virus-neutralizing sera in mice as tested on a panel of pseudotyped HIV-1 viruses on reporter TZM-bl cells. The VRA polypeptides mimic the epitope of a principle CD4 binding site required for the initial interaction of HIV-1 virus with host cell membrane and elicit antibodies targeting gp120 subunit. To strengthen the efficacy of the neutralization, however, it is still desirable to develop a more complex approach with production of polypeptides that would elicit antibodies blocking other crucial gp41 and gp120 epitopes within the HIV-1 envelope glycoprotein to avoid virus mutants escape from the immune surveillance.

DISCLOSURE OF THE INVENTION

The present invention provides polypeptides called herein MLA suitable for induction of HIV-1 virus-neutralizing antibodies which target "super candidate" bNAb 10E8 that is specific for MPER of gp41 subunit protruding from the viral envelope. The present invention also provides polypeptides called herein MLB and MLD that mimic V3-loop epitopes of highly potent neutralizing antibodies PGT126 and PGT121, respectively. The all polypeptides were obtained from a loop-randomized scaffold library designed on the structure of domain 10 of human contractile muscle protein myomesin-1. When the novel polypeptides are used as immunogens in experimental mice to stimulate the production of specific antibodies, the Env-specificity and virus-neutralizing activity of the hyperimmune sera tested on a panel of pseudotyped HIV-1 viruses of clades A, B, C, D and AE result in neutralization of most of the tested pseudoviruses in vitro.

The sequence of the parental human myomesin-1 domain 10 protein (PDB ID 6T3O) is as follows:

```
                                        (SEQ ID NO. 1)
    KSELAVEILEKGQVRFWMQAEKLSGNAKVNYIFNEKEIFE

GPKYKMHIDRNTGIIEMFMEKLQDEDEGTYTFQLQDGKAT

NHSTVVLVGDVFKKLQKEAEFQRQEWIRKQG
```

Amino acid residues in positions 21-24, 50-52 and 76-80 were randomized. These positions are shown in bold in SEQ IN NO. 1.

The present invention thus provides polypeptides having the length of up to 180 amino acids and containing a sequence selected from sequences identical or differing at most in 5 amino acids from the sequence:

```
                                        (SEQ ID NO. 2)
    KSELAVEILEKGQVRFWMQAX₂₁X₂₂X₂₃X₂₄GNAKVNYIFNEKEIFE

GPKYKMHIDX₅₀X₅₁X₅₂GIIEMFMEKLQDEDEGTYTFQLQX₇₆X₇₇X₇₈

X₇₉X₈₀NHSTVVLVGDVFKKLQKEAEFQRQEWIRKQG,
``` wherein $X_{21}X_{22}X_{23}X_{24}$ is selected from KAQQ (SEQ ID NO. 33), LSVF (SEQ ID NO. 34), ATPS (SEQ ID NO. 35), EIMW (SEQ ID NO. 36), DGSS (SEQ ID NO. 37), LLPL (SEQ ID NO. 38), WMWW (SEQ ID NO. 39), MNLY (SEQ ID NO. 40), MWRN (SEQ ID NO. 41), IMME (SEQ ID NO. 42), KHQL (SEQ ID NO. 43), HWQF (SEQ ID NO. 44), YAGN (SEQ ID NO. 45) and HGQW (SEQ ID NO. 46); $X_{50}X_{51}X_{52}$ is selected from RNT, IMF, GHE, PSW, RAN, YFW, ITL, QAM, DMR, WLW, QGE, VQY and VSL;

$X_{76}X_{77}X_{78}X_{79}X_{80}$ is selected from SHHLG (SEQ ID NO. 47), FMLMM (SEQ ID NO. 48), VILIL (SEQ ID NO. 49), IVTPL (SEQ ID NO. 50), DFIIW (SEQ ID NO. 51), MWSE (deletion) (SEQ ID NO. 52), LYYAW (SEQ ID NO. 53), MMIEY (SEQ ID NO. 54), WMTQT (SEQ ID NO. 55), PQLWL (SEQ ID NO. 56), EPIFL (SEQ ID NO. 57) and QTATY (SEQ ID NO. 58), optionally further having an affinity tag attached to the N-terminus or to the C-terminus of the sequence.

In some embodiments of the invention, the following combinations of the variables in SEQ ID NO. 2 are preferred:

$X_{21}X_{22}X_{23}X_{24}$ is selected from KAQQ (SEQ ID NO. 33), LSVF (SEQ ID NO. 34), ATPS (SEQ ID NO. 35), EIMW (SEQ ID NO. 36), DGSS (SEQ ID NO. 37), LLPL (SEQ ID NO. 38), WMWW (SEQ ID NO. 39), and MNLY (SEQ ID NO. 40);

$X_{50}X_{51}X_{52}$ is selected from RNT, IMF, GHE, PSW, RAN, YFW, ITL and QAM;

$X_{76}X_{77}X_{78}X_{79}X_{80}$ is selected from SHHLG (SEQ ID NO. 47), FMLMM (SEQ ID NO. 48), VILIL (SEQ ID NO. 49), IVTPL (SEQ ID NO. 50), DFIIW (SEQ ID NO. 51), MWSE (deletion) (SEQ ID NO. 52), LYYAW (SEQ ID NO. 53) and MMIEY (SEQ ID NO. 54).

Hereinafter, polypeptides having these variables are called MLA polypeptides.

In some embodiments of the invention, the following combinations of the variables in SEQ ID NO. 2 are preferred:

$X_{21}X_{22}X_{23}X_{24}$ is selected from MWRN (SEQ ID NO. 41), IMME (SEQ ID NO. 42) and KHQL (SEQ ID NO. 43);

$X_{50}X_{51}X_{52}$ is selected from RNT, DMR and WLW;

$X_{76}XX_{78}X_{79}X_{80}$ is selected from IVTPL (SEQ ID NO. 50) and WMTQT (SEQ ID NO. 55).

Hereinafter, polypeptides having these variables are called MLB polypeptides.

In some embodiments of the invention, the following combinations of the variables in SEQ ID NO. 2 are preferred:

$X_{21}X_{22}X_{23}X_{24}$ is selected from HWQF (SEQ ID NO. 44), YAGN (SEQ ID NO. 45) and HGQW (SEQ ID NO. 46);

$X_{50}X_{51}X_{52}$ is selected from QGE, VQY and VSL;

$X_{76}XX_{78}X_{79}X_{80}$ is selected from PQLWL (SEQ ID NO. 56), EPIFL (SEQ ID NO. 57) and QTATY (SEQ ID NO. 58).

Hereinafter, polypeptides having these variables are called MLD polypeptides.

Particularly preferred polypeptides of the present invention have the length of up to 180 amino acids and contain sequence selected from sequences identical or differing at most in 5 amino acids from the sequences:

```
                                      (SEQ ID NO. 3)
KSELAVEILEKGQVRFWMQAKAQQGNAKVNYIFNEKEIFE

GPKYKMHIDIMFGIIEMFMEKLQDEDEGTYTFQLQSHHLG

NHSTVVLVGDVFKKLQKEAEFQRQEWIRKQG (SEQ ID NO. 4)
KSELAVEILEKGQVRFWMQALSVFGNAKVNYIFNEKEIFE

GPKYKMHIDRNTGIIEMFMEKLQDEDEGTYTFQLQFMLMM

NHSTVVLVGDVFKKLQKEAEFQRQEWIRKQG (SEQ ID NO. 5)
KSELAVEILEKGQVRFWMQAATPSGNAKVNYIFNEKEIFE

GPKYKMHIDGHEGIIEMFMEKLQDEDEGTYTFQLQVILIL

NHSTVVLVGDVFKKLQKEAEFQRQEWIRKQG
```

-continued

```
                                      (SEQ ID NO. 6)
KSELAVEILEKGQVRFWMQAEIMWGNAKVNYIFNEKEIFE

GPKYKMHIDPSWGIIEMFMEKLQDEDEGTYTFQLQIVTPL

NHSTVVLVGDVFKKLQKEAEFQRQEWIRKQG (SEQ ID NO. 7)
KSELAVEILEKGQVRFWMQADGSSGNAKVNYIFNEKEIFE

GPKYKMHIDRANGIIEMFMEKLQDEDEGTYTFQLQDFIIW

NHSTVVLVGDVFKKLQKEAEFQRQEWIRKQG (SEQ ID NO. 8)
KSELAVEILEKGQVRFWMQALLPLGNAKVNYIFNEKEIFE

GPKYKMHIDYFWGIIEMFMEKLQDEDEGTYTFQLQMWSEN

HSTVVLVGDVFKKLQKEAEFQRQEWIRKQG (SEQ ID NO. 9)
KSELAVEILEKGQVRFWMQAWMWWGNAKVNYIFNEKEIFE

GPKYKMHIDITLGIIEMFMEKLQDEDEGTYTFQLQLYYAW

NHSTVVLVGDVFKKLQKEAEFQRQEWIRKQG (SEQ ID NO. 10)
KSELAVEILEKGQVRFWMQAMNLYGNAKVNYIFNEKEIFE

GPKYKMHIDQAMGIIEMFMEKLQDEDEGTYTFQLQMMIEY

NHSTVVLVGDVFKKLQKEAEFQRQEWIRKQG (SEQ ID NO. 11)
KSELAVEILEKGQVRFWMQAMWRNGNAKVNYIFNEKEIFE

GPKYKMHIDRNTGIIEMFMEKLQDEDEGTYTFQLQWMTQT

NHSTVVLVGDVFKKLQKEAEFQRQEWIRKQG (SEQ ID NO. 12)
KSELAVEILEKGQVRFWMQAIMMEGNAKVNYIFNEKEIFE

GPKYKMHIDDMRGIIEMFMEKLQDEDEGTYTFQLQIVTPL

NHSTVVLVGDVFKKLQKEAEFQRQEWIRKQG (SEQ ID NO. 13)
KSELAVEILEKGQVRFWMQAKHQLGNAKVNYIFNEKEIFE

GPKYKMHIDWLWGIIEMFMEKLQDEDEGTYTFQLQIVTPL

NHSTVVLVGDVFKKLQKEAEFQRQEWIRKQG (SEQ ID NO. 14)
KSELAVEILEKGQVRFWMQAHWQFGNAKVNYIFNEKEIFE

GPKYKMHIDQGEGIIEMFMEKLQDEDEGTYTFQLQPQLWL

NHSTVVLVGDVFKKLQKEAEFQRQEWIRKQG (SEQ ID NO. 15)
KSELAVEILEKGQVRFWMQAYAGNGNAKVNYIFNEKEIFE

GPKYKMHIDVQYGIIEMFMEKLQDEDEGTYTFQLQEPIFL

NHSTVVLVGDVFKKLQKEAEFQRQEWIRKQG
and
                                      (SEQ ID NO. 16)
KSELAVEILEKGQVRFWMQAHGQWGNAKVNYIFNEKEIFE

GPKYKMHIDVSLGIIEMFMEKLQDEDEGTYTFQLQQTATY

NHSTVVLVGDVFKKLQKEAEFQRQEWIRKQG,
``` optionally further having an affinity tag attached to the N-terminus or to the C-terminus of the sequence.

In some embodiments, the sequences of the present invention are identical to sequence SEQ ID NO. 2 (with the listed variable regions), or to sequences SEQ ID NO. 3 to SEQ ID NO. 16, optionally further having an affinity tag attached to the N-terminus or to the C-terminus of the sequence.

In some embodiments, the sequences of the present invention differ in at most 5 amino acids from sequence SEQ ID NO. 2 (with the listed variable regions), or from sequences SEQ ID NO. 3 to SEQ ID NO. 16, and optionally further have an affinity tag attached to the N-terminus or to the C-terminus of the sequence.

The term "differing at most in 5 amino acids" or "differ in at most 5 amino acids" means that 1 or 2 or 3 or 4 or 5 amino acids in the sequence are replaced (substituted) by other amino acids.

The term "have a length of up to 180 amino acids" means that the sequence SEQ ID NO. 2 (with the listed variable regions), or sequences SEQ ID NO. 3 to SEQ ID NO. 16, may be extended on C-terminus or on N-terminus or on both termini with a maximum total of 69 amino acids (or 70 amino acids). Preferably, the length of the polypeptide may be up to 160 or up to 140 or up to 120 amino acids.

In the present invention it has been found that polypeptides of this invention preferentially bind to variable regions of HIV-1 broadly neutralizing monoclonal antibodies 10E8 (MLA polypeptides), PGT126 (MLB polypeptides) and PGT121 (MLD polypeptides) as demonstrated by a higher binding affinity to these bNAbs in comparison to IgG isotype control and by competition assays. Use of polypeptides can be affected by a combination of an initial immunization dose and further booster doses, in which different versions of the polypeptides due to a substantial shape surface similarity can significantly increase production of neutralizing antibodies raised against the particular epitope-mimicking immunogen.

Affinity tags are typically used for purification of produced polypeptides, and then they can be cleaved or maintained in the sequence. Polypeptide tags may include, for example: ALFA-tag, AviTag, C-tag, polyglutamate tag, polyarginine tag, E-tag, FLAG-tag, HA-tag, His-tag, Myc-tag, NE-tag, Rho1D4-tag, S-tag, Softag1, Softag3, Spot-tag, Strep-tag, T7-tag, TC tag, Ty tag, V5 tag, VSV-tag, Xpress tag, Isopeptag, SpyTag, SnoopTag, Dog-Tag, SdyTag. Preferred tags are poly(his), FLAG, AviTag, HA, Myc, S-tag or V5-tag.

Polypeptides in the present invention are appropriate for the use in pharmaceutical technology, especially as mimicking recombinant protein ligands exploitable for development of more efficient vaccine preventing HIV-1 virus infection. To this goal it is beneficial to attach other helper proteins to the mentioned polypeptides of the present invention that can stimulate antibody production, for example serum albumin or heat shock protein hsp70. These helper proteins can be covalently linked to polypeptides forming a chimeric protein. Further possibilities are to modify the mentioned polypeptides by an attachment of helper N- or C-terminal sequences (tags), which allow their specific detection or their oriented immobilization to surface of carries such as nanoliposomes with enhancement of immunization efficacy. Such tags include, in preferred embodiments, affinity or detection tags such as poly(his), FLAG, AviTag, HA, Myc, S-tag or V5-tag.

Polypeptides in the present invention defined by amino acid sequence stimulate production of serum antibodies after being used for immunization of experimental animals. Hyperimmune sera of immunized animals suppressed infection of reporter cells by tested Env-pseudotyped viruses in the model system and this represents one of the key mechanisms of HIV-1 infection control and one of the aims for development of a preventative vaccine that is still not available in the market.

The major advantage of these polypeptides, in comparison to vaccines currently being tested, is their mimicking complexity for three different HIV-1 Env epitopes located at MPER of gp 41 and V3-loop of gp120. This allows neutralizing distinct prominent epitopes defined by the most efficient HIV-1 bNAbs 10E8, PGT121 and PGT126. Simultaneous elicitation of a portfolio of neutralizing antibodies by a host prevents virus mutants' escape from the immune surveillance. Practical advantage of these polypetides is their easy preparation, stability and absence of posttranslational modifications and this allows their easy biotechnological production in prokaryotic host cells *Escherichia coli* and their further utilization as vaccine antigens.

The present invention thus also provides a vaccine for prevention of HIV-1 virus infection, comprising polypeptide according to the present invention and/or conjugate according to the present invention as an active ingredient or as an auxiliary ingredient. In some embodiments, the vaccine may contain at least two polypeptides according to the present invention and/or at least two conjugates according to the present invention. Suitable auxiliary substances for formulation of vaccines are known in the art.

The present invention further provides a DNA sequence selected from the group comprising complementary DNA coding for the amino acid sequence of the polypeptides of the present invention The present invention further includes the use of said DNA sequence for the preparation of polypeptides or recombinant proteins produced in bacterial, yeast, insect, mammal or human host cells, and also these host cells, containing at least one DNA sequence of the present invention.

BRIEF DESCRIPTION OF DRAWINGS

FIGS. 1A-1B. Production characterization of human myomesin-1 domain 10. FIG. 1A) Analysis of protein fractions of human myomesin-1 domain 10 using SDS-PAGE gel electrophoresis, fractions from gel filtration chromatography on Superdex 75 10/300, M—molecular weight marker. FIG. 1B) Thermal stability of human myomesin-1 domain 10 measured by thermofluor thermal shift assay. Normalized thermal melting fluorescence curve (full line) and the first derivative of fluorescence curve versus temperature (dashed line). The melting point is given as the lowest point of the dashed curve.

FIGS. 2A-2B. Human Myomesin-1 Domain 10, a Loop-type Myomedin library concept. FIG. 2A) The crystal structure of the myomesin-1 domain 10 used for randomization (PDB ID 6t3o) as a part of the structures of a longer myomesin fragment (PDB ID 2y23). The domain 10 is shown with the randomized residues indicated as black spheres. FIG. 2B) A rotated view on domain 10 is shown in cartoon representation with the randomized residues indicated as black spheres.

FIGS. 4A-4D. Immunization of experimental mice with a panel of MLA variants induced serum antibodies specifically recognizing HIV-1 Env on the virus surface. FIG. 4A) Mice were immunized by the administration of four doses of individual MLA variants including wild-type (MyoWT). Sera were collected and tested in their reactivity with non-replicative HIV-1 viruses pseudotyped with FIG. 4B) Clade C Env (ZM109F) or FIG. 4C) Clade B Env (AC10.0, QH0692, RHPA) coated on ELISA plates. Statistical comparison was performed by ANOVA Kruskal-Wallis test with Dunn's post-test (* $P<0.05$,  $P<0.01$). The red asterisk indicates a comparison with MyoWT. FIG. 4D**) Sera from mice immunized with MLA092 and MLA025 Myomedins were tested for reactivity with RHPA-pseudotyped virus coated on ELISA panel in competition with 10E8 or VRC01.

Neutralization assays were performed using a set of HIV-1 Clade A, B, C, AE, and D pseudoviruses of Tier 2 or 3 with TZM-bl indicator cells. Serially diluted serum samples in duplicates were incubated with pseudoviruses. After the incubation pseudovirus with serum, TZM-bl cells at a density of 105 cells/ml were added, incubated, lysed, and after addition of substrate, luminescence was measured.

Figure 6:
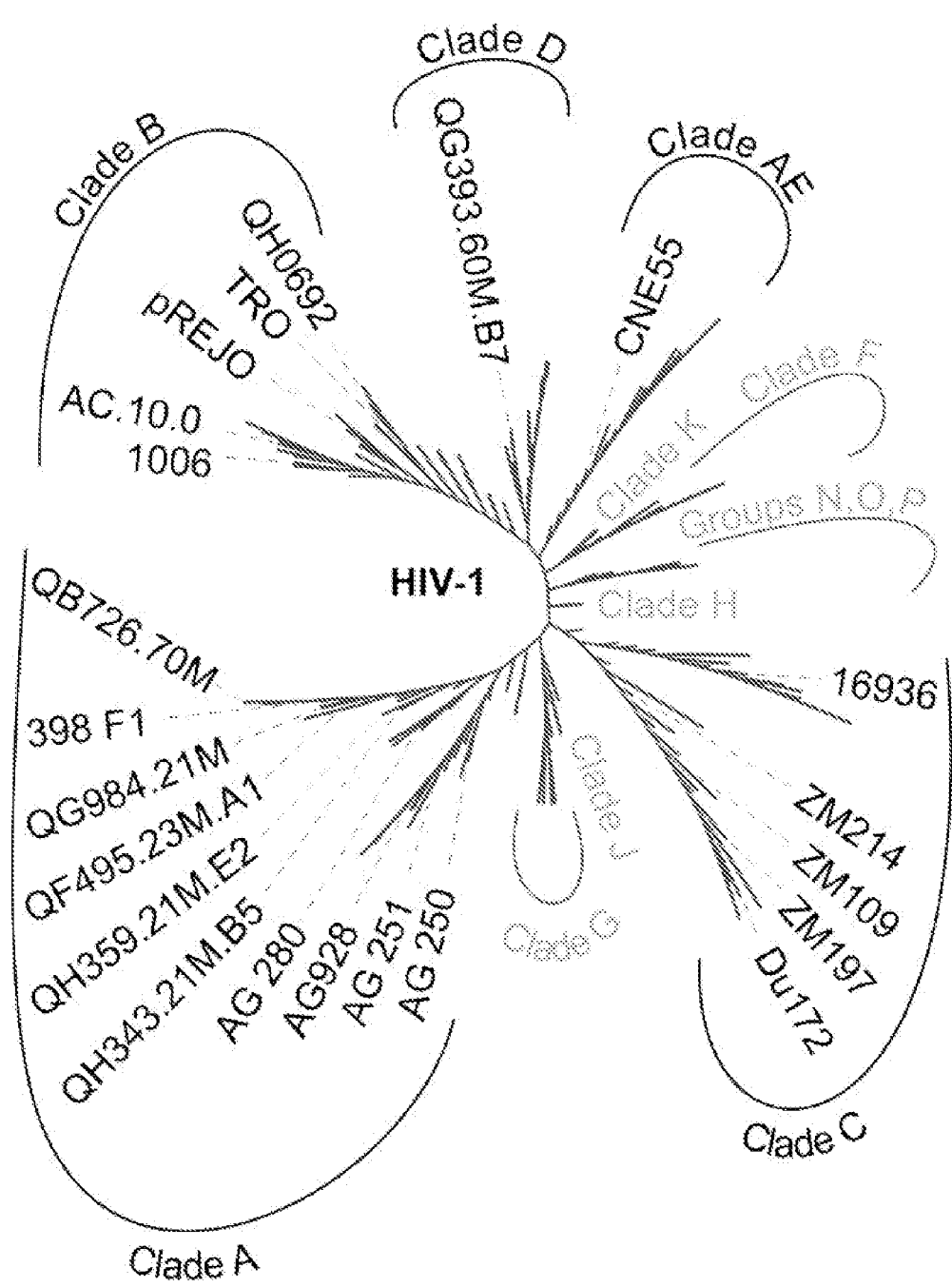

FIG. 6. An unrooted phylogenetic tree of 194 representative sequences from HIV-1 2019 Compendium of HIV-1 ENV genes (https://www.hiv.lan1.gov) enriched for 22 HIV-1 ENV sequences used in this analysis. HIV-1 strains are classified into four groups M, N, O and P. The major group M is further divided into nine genetically distinct subtypes A, B, C, D, AE, G, H, J, F and K. Each subtype contains hybrid viruses—circulating recombinant forms as a result of genetic material combination. For better orientation, only the 22 HIV-1 ENV sequences used in the analysis are visualized.

Figure 7:
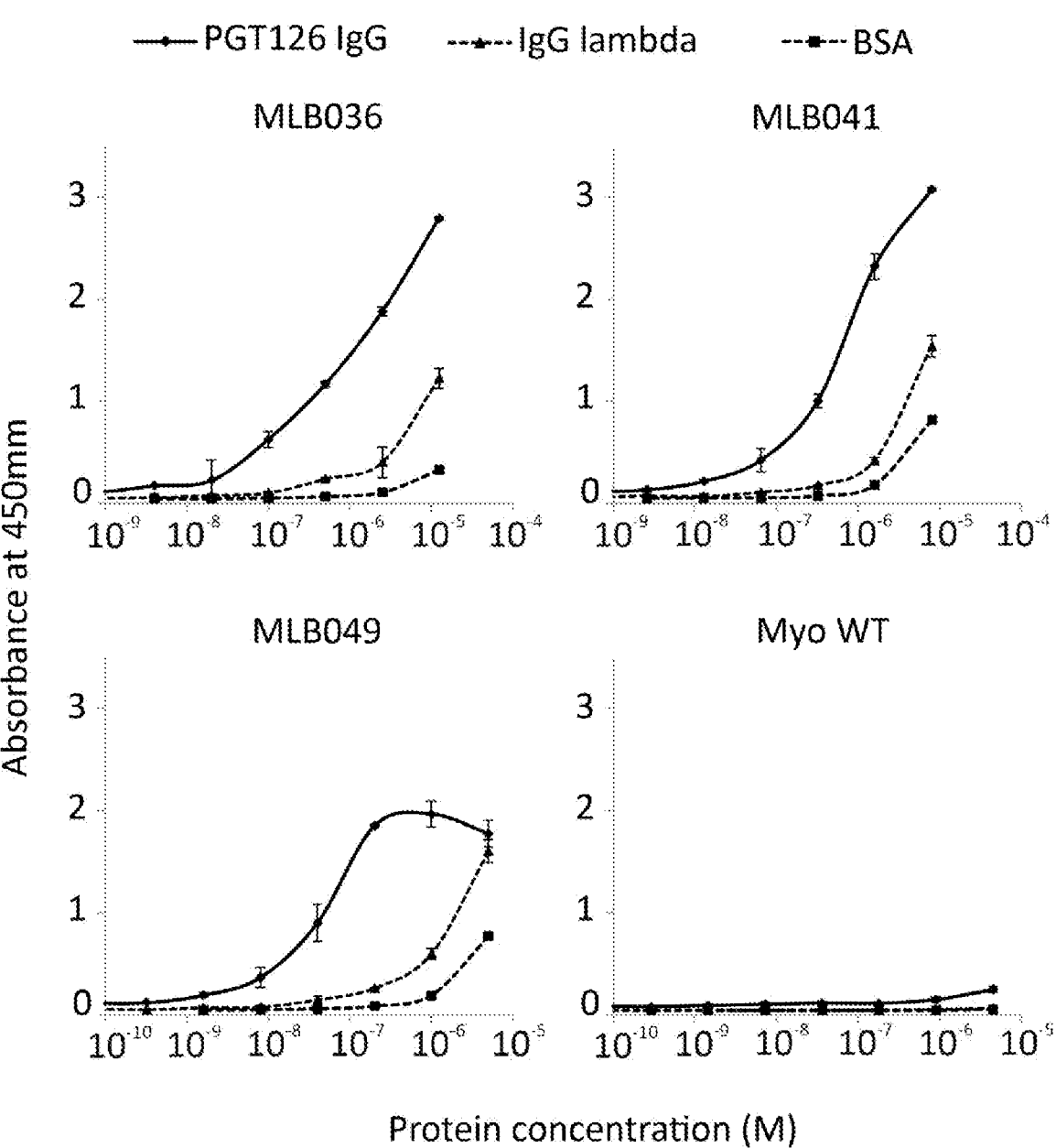

FIG. 7. Binding of MLB protein variants to PGT126 bNAb, IgG isotype control and BSA.

Three selected MLB clones were assayed in ELISA. Each point is shown as the mean value of duplicate with standard deviation.

Figure 8:
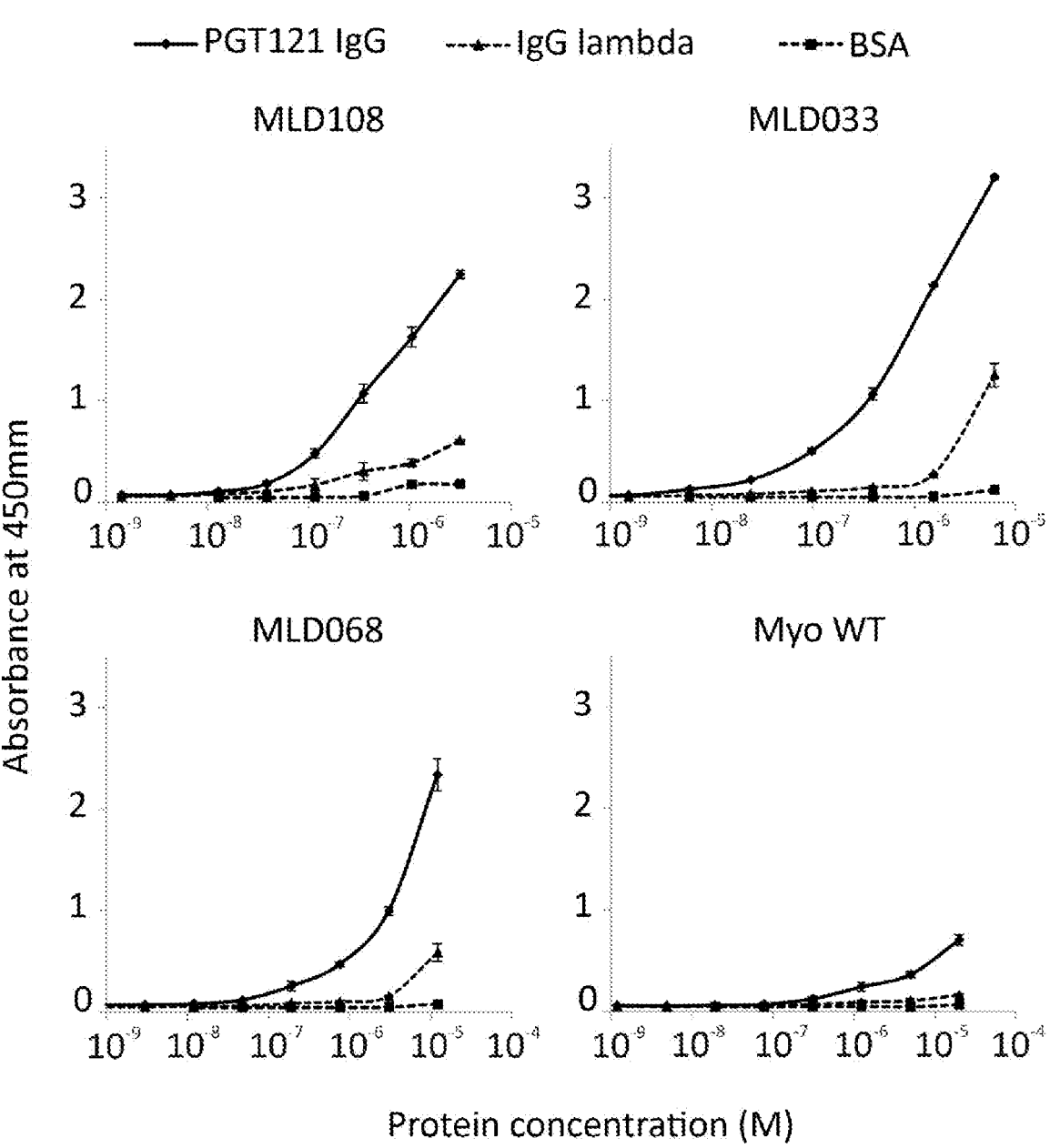

FIG. 8. Binding of MLD protein variants to PGT121 bNAb, IgG isotype control and BSA.

Three selected MLD clones were assayed in ELISA. Each point is shown as the mean value of duplicate with standard deviation.

Figure 9:
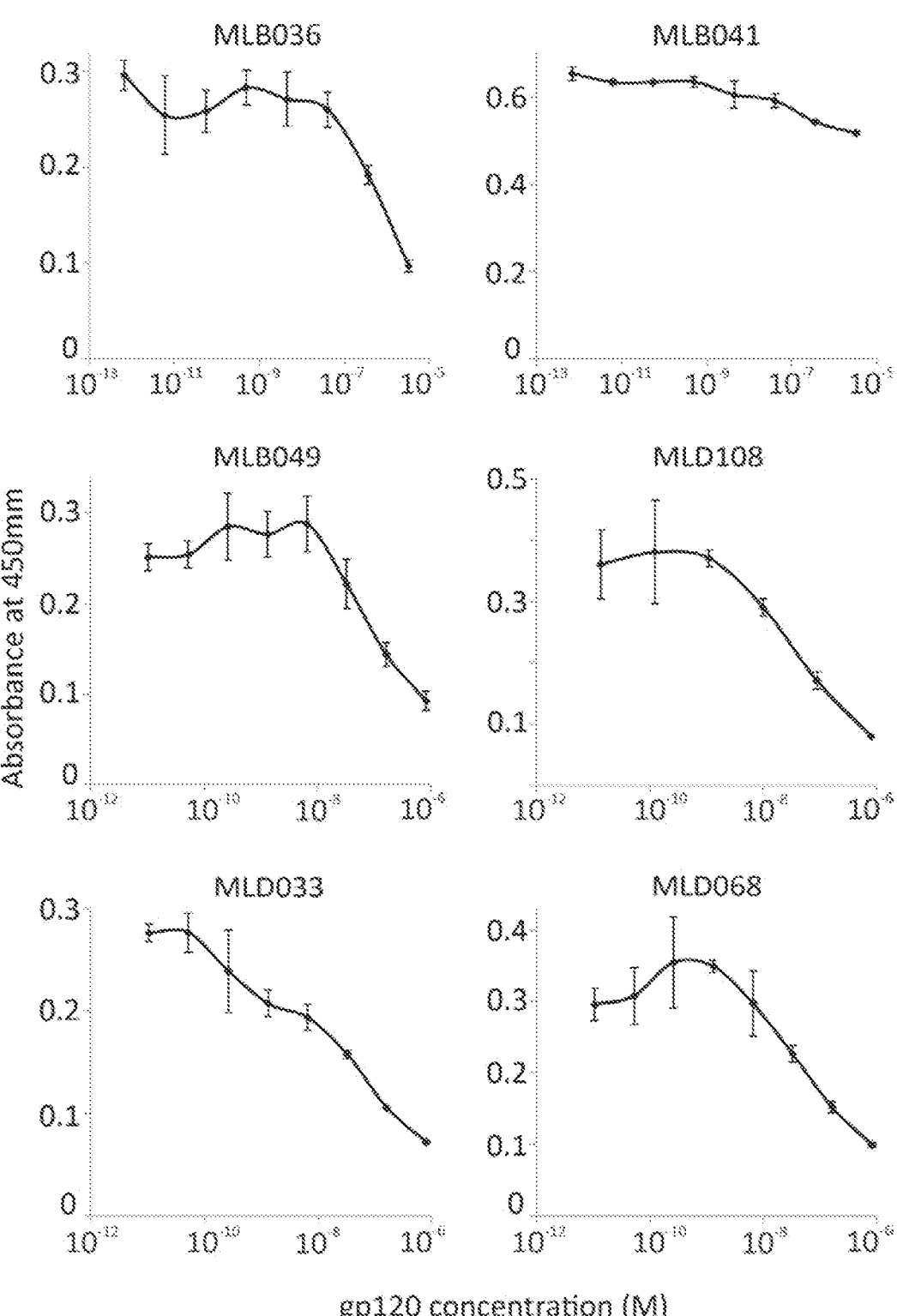

FIG. 9. Competition of MLB and MLD protein variants with HIV envelope glycoprotein gp120 for binding to PGT126 or PGT121 bNAb in ELISA. Their binding to PGT121 or PGT126 bNAb, respectively, was visualized by the anti-Flag M2 Ab-HRP conjugate or in the case of biotinylated protein by streptavidin-HRP. Each point is shown as the mean value of triplicates with standard deviation.

FIG. 10. Immunization of experimental mice with a panel of MLB variants induced serum antibodies specifically recognizing HIV-1 Env. Sera were collected and tested in their reactivity with multimerizing HIV-1 gp120 clade B consensus coated on ELISA plates. Antibody titers of IgG isotype were measured in ELISA. Statistical comparison was performed by ANOVA Kruskal-Wallis test with Dunn's post-test (* $P<0.05$).

FIG. 11. Binding of sera from mice immunized with MLB variants to HIV-1 multimeric gp120 is specifically inhibited by PGT126.

EXAMPLES OF CARRYING OUT THE INVENTION

In the following text, the polypeptides of the invention, derived from human Myomesin-1 domain 10, are called Myomedins.

Materials and Methods

Production of Human Myomesin-1 Domain 10

We produced domain 10 of myomesin-1 protein (MYOM1) in *E. coli* with N-terminal 6×His-tag and thrombin cleavage site. The protein was purified by Ni-NTA agarose and size-exclusion chromatography and its X-ray structure was solved to 1.8 Å resolution. The identified structure was deposited to the Protein Data Bank under accession code (PDB ID) 6t3o. Template DNA corresponding to the GenBank BC116183 was obtained from the Source BioScience (Nottingham, UK). Myomesin domain 10 was amplified by pair of primers (forward Myom10-F CATATGAAATCAGAGTTGGCAGTTGAAAT, SEQ ID NO. 17, reverse Myom10-R CAAGAATGGATCAG-GAAACAAGGTTAAGGATCC, SEQ ID NO. 18) inserting NdeI and BamHI restriction sites that were then used for the construct ligation into the pET28b vector. The final protein product contains a 6×His-tag and thrombin cleavage site at the N-terminus. Myomesin was produced in *E. coli* BL21 (QDE3) cells. Cells grew at 37° C. to OD600 of 0.6 in LB (Lysogeny Broth) then the expression of the protein was induced by 1 mM IPTG and cultivation continued for 4 hours more before the cells were harvested by centrifugation. The protein was purified using Ni-NTA agarose (Qiagen, Germany) under native conditions. Eluted protein fractions were pooled, concentrated and applied to the size-exclusion chromatography column Superdex 75 10/300 GL (GE Healthcare, UK) with running buffer 20 mM Tris, 50 mM NaCl pH 8.0. As documented in FIG. 1A, produced protein analyzed by SDS-PAGE gel electrophoresis corresponds to an expected molecular weight 16 kDa.

Thermal Shift Assay

Protein samples (0.1 mg/ml) and 5× Sypro Orange dye (Sigma Aldrich) were added into total volume 25 µl. Using the real-time PCR Detection System CFX96 Touch (Bio-Rad Laboratories), the proteins were incubated in a thermal gradient from 20° C. to 80° C. at increments of 0.5° C. and with 30 s-hold intervals.

The degree of protein unfolding was monitored by FRET (fluorescence resonance energy transfer) channel that captured the spectral properties of Sypro Orange unfolded protein complexes (excitation wavelength≈470 nm and emission wavelength≈570 nm). The data were analyzed by CFX Manager software and the melting temperatures were determined using the first derivative spectra. As shown in FIG. 1B, identified temperature melting point (Tm) corresponds to Tm 72° C. This demonstrates that myomesin-1 domain 10 maintains structure conformation and stability even when it is separated from the structural context of the myomesin filament.

Design of Combinatorial Library Based on Scaffold of Human Myomesin-1 Domain

The crystal structure of the myomesin-1 domain 10 (PDB ID 6t3o) is formed by 111 amino acids, which constitute the 2-layer sandwich of the immunoglobulin-like domain with 7 antiparallel D-strands and a terminal α-helix (FIG. 2A, B). The domain corresponds to the MY10 part of the myosin filament-linking protein myomesin-1 PDB ID 2y23 with 100% identity. To select a set of myomesin residues suitable for randomization we have performed in silico mutability screening of all amino acid residues. We have used the crystal structure of human myomesin-1 domain 10 (PDB ID 6t3o) and mutated all residues to all 20 amino acids using the PositionScan routine of FoldX program. According to the predicted change of free energy upon mutation, we have assigned to each residue a mutability score corresponding to several stabilizing substitutions. The score was used for the final selection of candidate residues trying to find a continuous patch of accessible surface residues with high mutability. This procedure led to a selection of following residues localized in loop regions of myomesin domain 10: E1267, K1268, L1269, S1270, R1296, N1297, T1298, D1322, G1323, K1324, A1325, and T1326, numbered according to the UniProt P52179 record. The residues selected for randomization are shown in FIG. 2B.

Myomedin Library Construction

Myomedin combinatorial library was assembled by a series of three PCR using Phusion High-Fidelity DNA Polymerase (NEB, Massachusetts, USA) using a list of primers and adaptors (see Table 1. below). 1st PCR (annealing temperature 65° C., 10 cycles) with 100 μM oligonucleotides MYOM-LP_n1F, MYOM-LP_2F and MYOM-LP_n2R resulted in 147 bp product, which was used in 2nd PCR (annealing temperature 59° C., 10 cycles) with 10 μM oligonucleotides MYOM-LP_1F and MYOM-LP_3R. 3rd PCR with 10 μM oligonucleotides L-for and L-rev was used to complete Myomedin sequence (333 bp). Furthermore, two additional PCR was used, 4th PCR with primers JOIN-F (adding ribosome binding site RBS), and JOIN-R and finally 5th PCR with primers T7B (adding T7 promoter) and TolAk joining Myomedin and TolA spacer (*E. coli* str. K-12). TolA spacer template for the 5th PCR was amplified using primers P7 link and TolA rev from isolated genomic DNA of *E. coli*. The resulted PCR product representing linear vector for in vitro transcription and translation (5'-T7 promotor-5' stem loop-RBS-Myomedin-TolAk-3' stem loop-3') was extracted from agarose gel and purified.

TABLE 1

List of oligonucleotides for combinatorial library assembly and ribosome display. Trinucleotide mixture of 19 amino acid codons (Ella Biotech GmbH, Martinsried, Germany) was used for the synthesis of randomized positions (bold) of a coding DNA strand (X01) and the complementary DNA strand (R01).

| | |
|---|---|
| MYOM-LP_n1F | AATGCCAAAGTGAACTATAT CTTCAACGAGAAAGAAATCT TCGAAGGTCCGAAATACAAAA TGCATATTG (SEQ ID NO. 19) |
| MYOM-LP_2F | GGTCCGAAATACAAAATGCA TATTGATX01X01X01GGCA TCATCGAAATGTTTATGG (SEQ ID NO. 20) |
| MYOM-LP_n2R | CAGCTGAAAGGTATAGGTGC CTTCATCTTCATCCTGCAGT TTTTCCATAAACATTTCGAT GATGCC (SEQ ID NO. 21) |
| MYOM-LP_1F | TCGTTTTTGGATGCAGGCAX 01X01X01X01GGTAATGCC AAAGTGAACTATATCTTC (SEQ ID NO. 22) |

TABLE 1-continued

List of oligonucleotides for combinatorial library assembly and ribosome display. Trinucleotide mixture of 19 amino acid codons (Ella Biotech GmbH, Martinsried, Germany) was used for the synthesis of randomized positions (bold) of a coding DNA strand (X01) and the complementary DNA strand (R01).

| | |
|---|---|
| MYOM-LP_3R | CCAGAACAACGGTTGAATGA TTR01R01R01R01R01CTG CAGCTGAAAGGTATAGGTGC (SEQ ID NO. 23) |
| L-for | AAAAGCGAGCTGGCCGTGGA AATTCTGGAAAAAGGTCAGG TTCGTTTTTGGATGCAGGCA (SEQ ID NO. 24) |
| L-rev | ACCCTGTTTACGAATCCATT CTTGGCGCTGAAATTCTGCT TCTTTTTGCAGTTTTTTGAA CACGTCACCAACCAGAACAA CGGTTGAATGATT (SEQ ID NO. 25) |
| JOIN-F | CTATAGGGAGACCACAACGG TTTCCCTCTAGAAATAATTT TGTTTAACTTTAAGAAGGAG ATATACATATGAAAAGCGAG CTGGCCG (SEQ ID NO. 26) |
| JOIN-R | GAACCGACCGCGGATCCACC CTGTTTACGAATCCATTCTT (SEQ ID NO. 27) |
| T7B | ATACGAAATTAATACGACTC ACTATAGGGAGACCACAACG G (SEQ ID NO. 28) |
| TolAk | CCGCACACCAGTAAGGTGTG CGGTTTCAGTTGCCGCTTTC TTTCT (SEQ ID NO. 29) |
| P7 link | GGATCCGCGGTCGGTTCGA (SEQ ID NO. 30) |
| TolA rev | TTTCCGCTCGAGCTACGGTT TGAAGTCCAATGGCGC (SEQ ID NO. 31) |
| His-Myo-F | CAGTCCATGGGCAGCAGCCA TCATCATCATCATCACAGCA GCGGCAAAAGCGAGCTGGCC G (SEQ ID NO. 32) |

Antibodies Used for Selection.

Broadly neutralizing human anti-HIV-1 Env monoclonal antibodies 10E8, PGT121, and PGT126 were obtained from the NIH AIDS Reagent Program (Division of AIDS, NIAID, NIH, Germantown, MD). 10E8, PGT121, or PGT126 IgG were used as a target protein for ribosome display and in ELISA applications (stored as 1 mg/mL aliquoted source stock at −80° C.). Human IgG1 with κ or λ light chain (light chain was used as complementary to tested bNAb, purified myeloma protein, Sigma-Aldrich, St. Luis, MO) was chosen as an isotype control for library preselection in ribosome display and as a negative control in ELISA (stored aliquoted as 1 mg/mL source stock at −20° C.).

Ribosome Display Selection

Myomedin combinatorial library was used for in vitro transcription/translation and further ribosome display (RD) selection. Three-round RD selections were performed, 96-well Polysorp plates (NUNC, Denmark) were coated by 10E8 IgG1 diluted in coating 100 mM bicarbonate/carbonate solution (pH 9.6) at a concentration according to the adjusted stringency in each round of RD selection procedure: 1st round—25 µg/mL, 2nd round—10 µg/mL and 3rd round—10 µg/mL. Pre-selection procedure was performed in wells coated with human IgG1 lambda antibody at a constant concentration of 25 µg/mL in each round. Final cDNA after the third round of the selection was amplified by PCR with primers His-Myo-F and JOIN-R. Cleaved PCR product (NcoI, BamHI) was introduced into a pET-28b vector carrying V5 tag sequence downstream of Myomedin cDNA and cloned in *E. coli* XL1 blue host cells. The same method was used to select proteins binding to PGT121 and PGT126 IgG.

12

Production of Myomedin Variants

Myomedin protein variants designated MLA, MLB and MLD (see Table 2.) were produced as 16 kDa recombinant proteins with N-terminal His6 tag and C-terminal V5 tag (His6-Myomedin-V5) in *E. coli* BL21 (DE3) strain in LB medium containing kanamycin (60 µg/mL). Protein production was induced by 1 mM IPTG after the culture reached the optical density OD600=0.6, cells were further cultivated, shaken at 250 RPM, 25° C. for 4 hours after induction. Harvested cells were sonicated in TN buffer (50 mM Tris, 150 mM NaCl, pH 8.0), centrifuged (40 000×g, 20 min. 4° C.) and subsequently, bacterial lysates were analyzed or protein was purified on Ni-NTA agarose column.

TABLE 2

Table of MLA, MLB and MLD sequences. Sequence comparison of the protein variants with parental non-randomized MyoWT protein. Grey boxes indicate the loop stretches with 12 positions at which the residues of MyoWT were randomized. Other residues of the 111 amino acid Myomedin scaffold protein were not mutated in all shown binding proteins.

| | L1 | | | | | L2 | | | | L3 | | | | | |
|---|---|---|---|---|---|---|---|---|---|---|---|---|---|---|---|
| | 21 | 22 | 23 | 24 | | 50 | 51 | 52 | | 76 | 77 | 78 | 79 | 80 | SEQ ID NO. |
| MyoWT | E | K | L | S | . . . | R | N | T | | D | G | K | A | T | 1, 59, 60 |
| MLA016 | K | A | Q | Q | . . . | I | M | F | . . . | S | H | H | L | G | 3, 33, 47 |
| MLA024 | L | S | V | F | . . . | R | N | T | . . . | F | M | L | M | M | 4, 34, 48 |
| MLA025 | A | T | P | S. | . . . | G | H | E | . . . | V | I | L | I | L | 5, 35, 49 |
| MLA092 | E | I | M | W | . . . | P | S | W | . . . | I | V | T | P | L | 6, 36, 50 |
| MLA093 | D | G | S | S | . . . | R | A | N | . . . | D | F | I | I | W | 7, 37, 51 |
| MLA132 | L | L | P | L | . . . | Y | F | W | . . . | M | W | S | E | — | 8, 38, 52 |
| MLA158 | 3 | M | N | W | . . . | I | T | L | . . . | L | Y | Y | A | W | 9, 39, 53 |
| MLA159 | M | N | L | Y | . . . | Q | A | M | . . . | M | M | I | E | Y | 10, 40, 54 |
| MLB036 | M | W | R | N | . . . | R | N | T | . . . | W | M | T | Q | T | 11, 41, 55 |
| MLB041 | I | M | M | E | . . . | D | M | R | . . . | I | V | T | P | L | 12, 42, 50 |
| MLB049 | K | H | Q | L | . . . | W | L | W | . . . | I | V | T | P | L | 13, 43, 50 |
| MLD033 | H | W | Q | F | . . . | Q | G | E | . . . | P | Q | L | W | L | 14, 44, 56 |
| MLD068 | Y | A | G | N | . . . | V | Q | Y | . . . | E | P | I | F | L | 15, 45, 57 |
| MLD108 | H | G | Q | W | . . . | V | S | L | . . . | Q | T | A | T | Y | 16, 46, 58 |

ELISA

Cell lysates of *E. coli* clones producing Myomedin protein variants were prepared using sonicator (Misonix 3000). Polysorp plate (NUNC) was coated with 10E8, PGT121 or PGT126 IgG (5 µg/mL) or IgG1 lambda (5 µg/mL) in coating buffer (100 mM bicarbonate/carbonate solution, pH 9.6) at 7° C. overnight. Next day, the plate was washed by PBST solution (PBS buffer containing 0.05% Tween, pH 7.4) and wells were blocked by PBSTB (PBS buffer pH 7.4, containing 0.05% Tween and 1% BSA). The lysate samples (diluted 33×) purified protein variants as well as Myomedin-wt negative control diluted in PBSTB were applied. Binding of the Myomedin variants was detected using anti-V5 tag-HRP conjugate in PBSTB (1:10 000, Abcam, Cambridge, UK). Results were visualized by the enzymatic reaction of HRP with TMB-Complete 2 substrate (TestLine Clinical Diagnostics s.r.o., Brno, Czech Republic), the reaction was stopped by 2 M sulfuric acid and absorbance at 450 nm was measured.

Myomedin Variants Induce Serum Antibodies Recognizing Env Glycoproteins on Pseudotyped HIV-1 Viruses.

Eight MLA protein variants 016, 024, 025, 092, 093, 132, 158 and 159 were expressed and purified as recombinant proteins and used for immunization of experimental mice by i.d. route with Freund's adjuvant by four consecutive antigen injections, according to the schedule presented in FIG. 4A. MPER-specific reaction was evaluated on pseudoviruses coated on ELISA panel as the presence of membrane surrounding the gp41 is necessary to MPER epitope. Four pseudoviruses—one Clade C Env (ZM109F) (FIG. 4B) and three Clade B Env (AC10.0, QH0692, RHPA) (FIG. 4C) were assayed on ELISA. The experiment identified significant binding for MLA 025, 092, 093, 158 and 159 at least with one pseudotyped virus (FIG. 4B, C) when compared with wild-type Myomedin (MyoWT). MyoWT did not elicit detectable Env-pseudovirus specific serum response. To further confirm MPER specificity of sera binding, we performed an ELISA competition assay where the binding of sera to selected pseudovirus from Clade B (here RHPA) competed with a serial dilution of 10E8 as an original specific target used for all MLA variants selection (FIG. 4D). 10E8 in concentration 2 µg/ml completely inhibited all tested hyperimmune sera reactivity. When irrelevant bNAb was used for competition (here VRC01) no competition was observed even at concentration 3.33 µg/ml. As negative controls, naive sera and Myomedin wild type-immunized mice sera were tested in the same assay and no binding of sera to RHPA was observed irrespective to titration of 10E8 as a competitor (FIG. 4D). 10E8 serially diluted to achieve final concentrations 2; 1; 0.5; 0.25; 0.125; 0.0625; and 0 µg/ml in blocking buffer was applied with individual MLA092- or MLA025-immunized mouse sera diluted 1:400. After washing, the plates were incubated with rabbit anti-mouse IgG HRP-conjugated antibody, developed with a substrate and O.D. 492 nm was measured. VRC01 antibody was applied in control reaction, as irrelevant antibody, at final 3.33; 1; 0.33; 0.1; 0.033; and 0 µg/ml analogously to 10E8. In separate experiment 10E8 at indicated concentration was applied with individual MyoWT-immunized or naive mouse sera diluted 1:400 as the control. All experiments were performed in triplicates. Mean values are indicated by horizontal lines.

Immunization of Experimental Mice

Female BALB/c mice, 6-8 weeks old, 18-22 g (AnLab, Brno, Czech Republic), were used for all immunization experiments. Animals were housed under standard conditions according to ARRIVE guidelines. The immunization experiments were approved by the Ethics Committee of the Faculty of Medicine and Dentistry (Palacky University, Olomouc, Czech Republic) and the Ministry of Education, Youth and Sports, Czech Republic (MSMT-9487/2019-3). All mice were immunized four times. Pre-immune (naïve) sera were collected before the first immunization. All immunizations were performed by intradermal route with an equal dose of 10 µg of individual Myomedin variant (diluted in 50 µl of DPBS) mixed with 50 µl of Freund's adjuvant (Sigma Aldrich, St. Louis, MO, USA) per mouse per one immunization.

Neutralization Titration of Sera from MLA-Immunized Mice.

Figure 3:
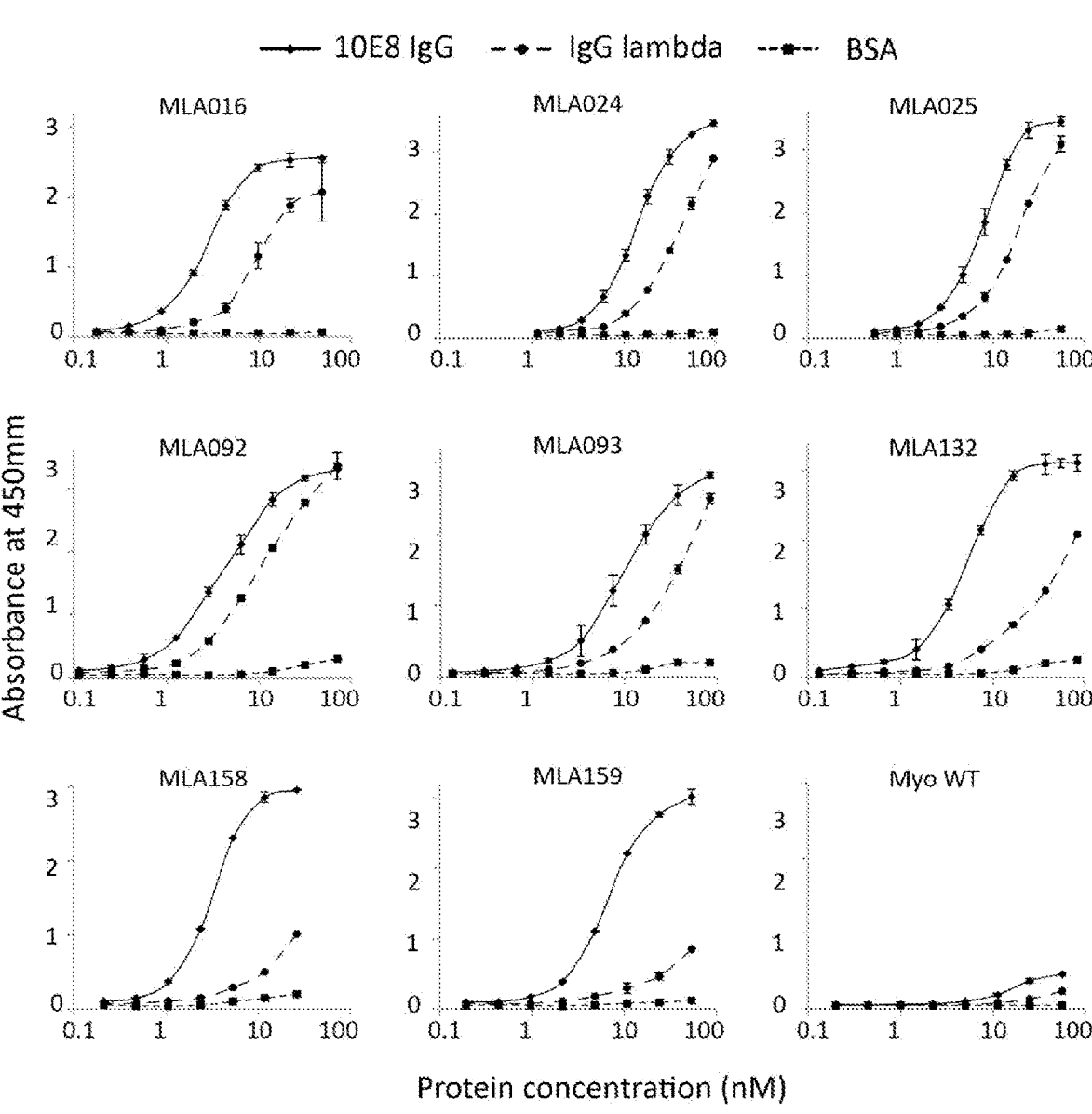
FIG. 3. Binding of MLA protein variants to 10E8 bNAb, IgG isotype control and BSA. Myomedin variants of eight selected MLA clones in the form of purified fusion proteins with N-terminal polyhistidine tag and C-terminal V5 tag produced in *E. coli* BL21 (DE3) were assayed in ELISA, the parental non-randomized Myomedin was used as a negative control. Binding to immobilized 10E8 bNAb (labeled as 10E8 IgG), IgGli isotype (labeled as IgG lambda) and BSA was detected by anti-V5 Ab-HRP conjugate. Each point is shown as the mean value of triplicates with standard deviation.
Figure 5:
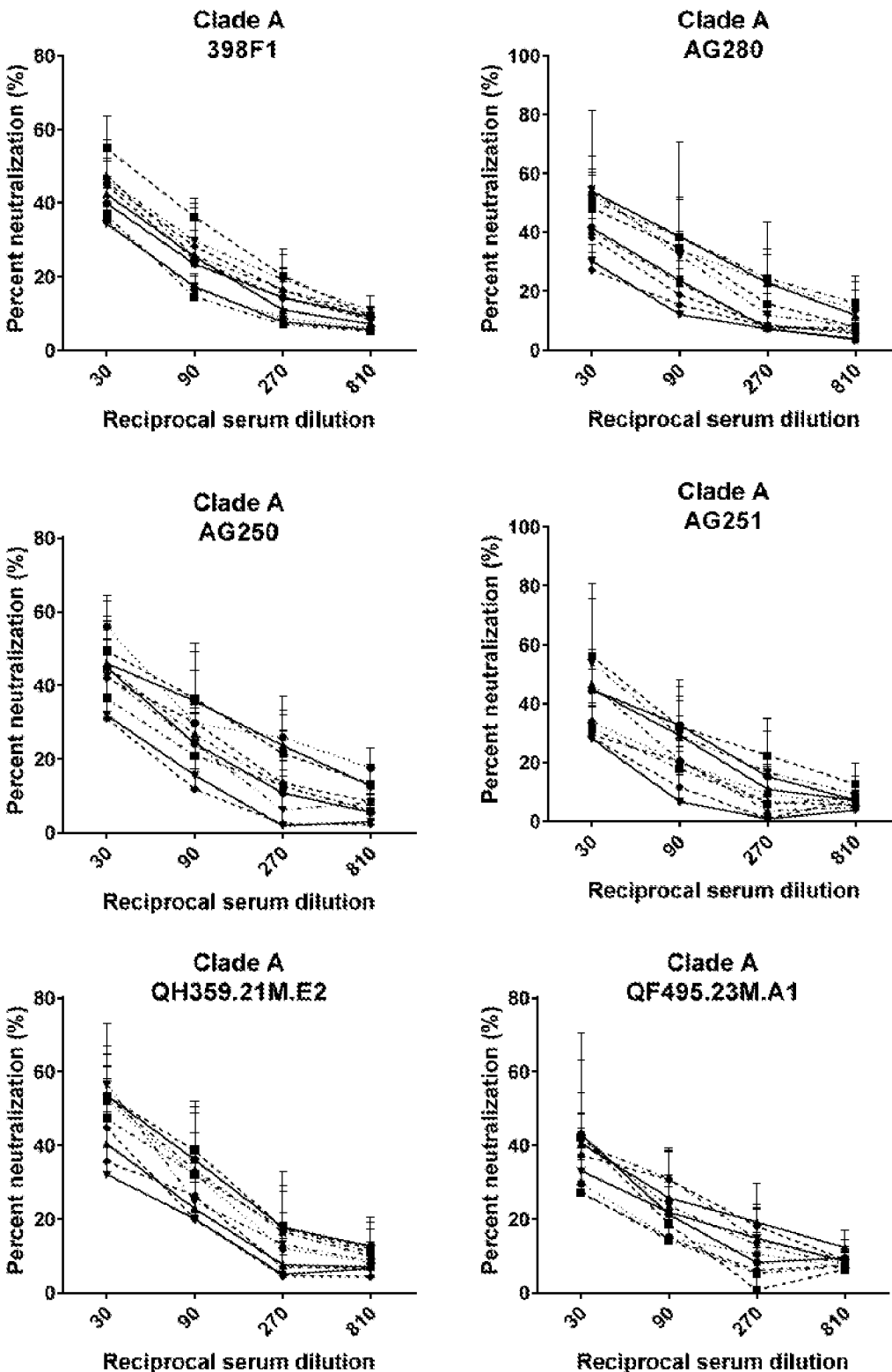
FIG. 5. Neutralization titration of sera from MLA-immunized mice.

Mice were immunized by the administration of four doses of individual MLA variants including wild-type (MyoWT). Each group consisted of five animals. Neutralization assays were performed using a set of HIV-1 Clade A, B, C, AE, and D pseudoviruses of Tier 2 or 3 with TZM-bl indicator cells. Serially diluted serum samples in duplicates were incubated with pseudoviruses. The pseudoviruses load was set to achieve approximately 150 000 RLU in 150 µl of DMEM in the absence of sera. After the incubation pseudovirus with serum, TZM-bl cells at a density of 105 cells/ml were added, incubated, lysed, and after addition of substrate, luminescence was measured. Results are indicated in FIG. 5. The 22 HIV-1 ENV sequences used in the analysis are visualized in FIG. 6.

HIV-1 Env Specific Binding Antibodies Determination

Reactivity of binding antibodies targeting Env was measured by ELISA using pseudotyped viruses prepared for virus neutralization assay (MLA polypeptides see below) or recombinant HIV-1 consensus clade B multimerizing polypeptides (MLB and MLD). To remove fetal bovine serum pseudotyped viruses were first ultracentrifuged for 3 hours at 50.000 g at 4° C. and resuspended in PBS. MaxiSorp ELISA plates (NUNC, Roskilde, Denmark) were coated with pseudotyped viruses diluted in PBS overnight at 4° C. Coating with recombinant gp120 was performed under the same conditions. Plates were washed with PBS and blocked with 1% BSA/PBS for 3 hours at room temperature. Mouse sera were serially diluted in blocking buffer in duplicates and incubated overnight at 4° C. Plates were washed with PBS and bound antibodies targeting Env were determined by incubating with anti-mouse IgG secondary antibody conjugated with horseradish peroxidase diluted in blocking buffer for 3 hours. Plates were washed and the signal was developed with O-phenylenediamine-$H_2O_2$ substrate. The reaction was stopped with IM sulphuric acid. The absorbance was quantified at 492 nm by ELISA reader.

Competition ELISA

Plates were coated with the selected HIV-1 pseudotyped virus or recombinant HIV-1 multimerizing gp120 protein as described in the previous method of Env-specific binding antibodies determination. 10E8, PGT126, or PGT121 antibodies were serially diluted in blocking buffer and applied in doublets with mouse hyperimmune sera diluted accordingly. Plates were washed and bound mouse antibodies were detected by rabbit anti-mouse IgG secondary antibody conjugated with horseradish peroxidase diluted in blocking buffer. Signal was developed and measured as described above.

Virus Preparation

Pseudotyped viruses were prepared using HEK293/17 cell line grown in 75 cm2 at 60-80% confluency co-transfected with 4 µg of plasmid coding Env and 8 µg of plasmid coding pSG3deltaEnv mixed with 48 µl of transfection reagent FuGene6 (Promega, Madison, WI, USA) in 12 ml of culture medium. After 2 days, produced pseudotyped viruses in culture medium were harvested, filtered and stored at 80° C. until used.

Virus Neutralization Assay

Virus neutralization assay was done using various pseudotyped viruses of clades A, B, C, D and AE. Murine leukemia virus (MULV)-pseudotyped virus containing the Env of MULV with the same backbone vector as all HIV-1-pseudotyped viruses (pSG3AEnv) was used as a negative control. Before the assay, mouse sera were heat-inactivated for 1 hour at 56° C. Sera in duplicates were serially diluted in 100 μl of culture medium in 96-well plates and incubated with 50 μl of pseudotyped viruses at 150.000 RLU for 90 minutes at 37° C. Then, 10.000 TZM-bl cells stably expressing CD4 receptor, CCR5, CXCR4 co-receptors and containing genes for luciferase and β-galactosidase under control of HIV-1 promotor (NIH AIDS Research and Reference Reagent Program, Division of AIDS, NIAID, NIH) in 50 μl of culture medium were added into each well and incubated for 48 hours at 37° C. in 5% $CO_2$ atmosphere. 150 μl of culture medium was removed and 100 μl of lysis buffer containing luciferin (Promega) was added. After 2 minutes, 100 μl of lysate was transferred into a black 96-well plate and luminescence was measured using HP luminometer. This method was used to measure neutralization activity of MLA immunized sera (Table 3.) and MLB immunized sera (Table 4.).

TABLE 3

Neutralization activity of MLA-immunized mice sera. Values represent the reciprocal serum dilution which resulted in 50% virus neutralization. Relative mean neutralization dil. represents mean values of detected titers among all tested pseudoviruses. No. of neutralized PVs indicates the sum of pseudoviruses neutralized at reciprocal titer higher than 30. Murine leukemia virus (MULV) was used in neutralization assay as a control. Pseudotyped viruses used for analyses were chosen to cover the phylogenetic tree of HIV-1 Env.
Reciprocal serum dilution resulted in 50% virus neutralization

| | | Myomedin MLA | | | | | | | | | |
| Clade | Pseudovirus | 016 | 024 | 025 | 092 | 093 | 132 | 158 | 159 | WT | Naïve |
|---|---|---|---|---|---|---|---|---|---|---|---|
| AE | CNE55 | < | < | 41 | < | < | 35 | < | < | < | < |
| A | 398F1 | < | < | < | 35 | < | < | < | < | < | < |
| | AG280 | 35 | 31 | < | 35 | < | < | < | 32 | < | < |
| | QG984.21M.A3 | < | < | 35 | < | < | 33 | 38 | < | < | < |
| | AG250 | 33 | < | < | < | < | < | 37 | < | < | < |
| | AG251 | < | < | < | 43 | < | < | 46 | < | < | < |
| | QB726.70M.C4 | < | < | 38 | < | < | < | < | < | < | < |
| | QH359.21M.E2 | 34 | < | 45 | 42 | < | 36 | 38 | < | < | < |
| | QF495.23M.A1 | < | < | < | < | < | < | < | < | < | < |
| | AG928 | < | < | < | 34 | < | 35 | < | 34 | < | < |
| | QH343.21M.B5 | < | < | < | 32 | 44 | 57 | < | < | < | < |
| B | AC.10.0 | < | < | 30 | 56 | < | 59 | 92 | 78 | < | < |
| | QH0692 | < | < | 45 | 57 | < | 40 | 75 | 53 | < | < |
| | pREJO | 33 | < | 60 | < | < | < | < | < | < | < |
| | 1006 | < | < | < | 42 | < | 35 | < | < | < | < |
| | TRO | 45 | < | < | < | < | < | 42 | < | < | < |
| C | ZM197 | < | < | < | 44 | < | < | 63 | 43 | < | < |
| | ZM214 | < | < | < | < | < | < | < | < | < | < |
| | ZM109 | 52 | 47 | 72 | 52 | < | 37 | 38 | < | < | < |
| | Du172 | 58 | 37 | 62 | 74 | < | 57 | 60 | < | < | < |
| | 16936 | < | < | < | < | < | < | < | < | < | < |
| D | QG393.60M.B7 | < | < | < | < | < | < | < | < | < | < |
| CTRL | MULV | < | < | < | < | < | < | < | < | < | < |
| | Relative mean neutralization dil. | 41 | 38 | 47 | 45 | 44 | 42 | 52 | 48 | | |
| | No. of neutralized PVs | 7 | 3 | 9 | 12 | 1 | 10 | 10 | 5 | | |

TABLE 4

Neutralization activity of MLB- and MLD-immunized mice sera. Values represent the reciprocal serum dilution which resulted in 50% virus neutralization. Relative mean neutralization dil. represents mean values of detected titers among all tested pseudoviruses. No. of neutralized PVs indicates the sum of pseudoviruses neutralized at reciprocal titer higher than 30. Murine leukemia virus (MULV) was used in neutralization assay as a control. Pseudotyped viruses used for analyses were chosen to cover the phylogenetic tree of HIV-1 Env.
Reciprocal serum dilution resulted in 50% virus neutralization

| | | MLB - PGT126 | | | MLD - PGT121 | | | | |
| Clade | Pseudovirus | 036 | 041 | 049 | 033 | 068 | 108 | WT | Naïve |
|---|---|---|---|---|---|---|---|---|---|
| AE | CNE55 | < | < | < | < | < | < | < | < |
| A | 398F1 | < | 35 | < | < | < | < | < | < |
| | AG280 | 35 | 42 | 38 | < | < | 39 | < | < |
| | QG984.21M.A3 | 31 | 33 | < | < | < | < | < | < |

TABLE 4-continued

Neutralization activity of MLB- and MLD-immunized mice sera. Values represent the
reciprocal serum dilution which resulted in 50% virus neutralization. Relative
mean neutralization dil. represents mean values of detected titers among all
tested pseudoviruses. No. of neutralized PVs indicates the sum of pseudoviruses
neutralized at reciprocal titer higher than 30. Murine leukemia virus (MULV)
was used in neutralization assay as a control. Pseudotyped viruses used for
analyses were chosen to cover the phylogenetic tree of HIV-1 Env.
Reciprocal serum dilution resulted in 50% virus neutralization

| Clade | Pseudovirus | MLB - PGT126 | | | MLD - PGT121 | | | | |
|---|---|---|---|---|---|---|---|---|---|
| | | 036 | 041 | 049 | 033 | 068 | 108 | WT | Naïve |
| | AG250 | < | < | < | < | < | < | < | < |
| | AG251 | < | < | < | < | < | < | < | < |
| | QB726.70M.C4 | < | < | < | < | < | < | < | < |
| | QH359.21M.E2 | 37 | 45 | 33 | < | < | 35 | < | < |
| | QF495.23M.A1 | 43 | 49 | 45 | < | < | 38 | < | < |
| | AG928 | < | < | < | < | < | < | < | < |
| | QH343.21M.B5 | 38 | < | < | < | < | 32 | < | < |
| B | AC.10.0 | < | < | < | < | < | < | < | < |
| | QH0692 | < | 45 | 42 | < | < | 35 | < | < |
| | pREJO | 38 | 53 | < | < | < | 37 | < | < |
| | 6535 | 41 | < | 32 | < | < | < | < | < |
| | TRO | 31 | 35 | 34 | < | < | 34 | < | < |
| C | ZM197 | < | < | < | < | < | < | < | < |
| | ZM214 | < | < | < | < | < | < | < | < |
| | ZM109 | 33 | < | 32 | < | 33 | 38 | < | < |
| | Du172 | < | < | < | < | < | < | < | < |
| | 16936 | 51 | < | 33 | < | 31 | 35 | < | < |
| D | QG393.60M.B7 | < | < | < | < | < | < | < | < |
| CTRL | MULV | < | < | < | < | < | < | < | < |
| | Relative mean neutralization dil. | 37.8 | 42.1 | 36.1 | 30 | 32 | 35.8 | | |
| | No. of neutralized PVs | 10 | 8 | 8 | 0 | 2 | 9 | | |

Binding of MLB Protein Variants to PGT126 Broadly Neutralizing Antibody.

Three selected MLB clones 036, 041 and 049 in the form of purified fusion proteins with N-terminal polyhistidine tag and C-terminal V5 tag produced in *E. coli* BL21 (DE3) were assayed in ELISA, the parental non-randomized Myomedin was used as a negative control. Binding to immobilized PGT126 bNAb (labeled as PGT126 IgG), IgG1λ isotype (labeled as IgG lambda) and BSA was detected by anti-V5 Ab-HRP conjugate. Each point is shown as the mean value of duplicate with standard deviation. Results are presented in FIG. 7.

Binding of MLD Protein Variants to PGT121 Broadly Neutralizing Antibody.

Selected MLD clones 108, 033 and 068 in the form of purified fusion proteins with N-terminal polyhistidine tag and C-terminal V5 tag produced in *E. coli* BL21 (DE3) were assayed in ELISA, the parental non-randomized Myomedin was used as a negative control. Binding to immobilized PGT121 bNAb (labeled as PGT121 IgG), IgGli isotype (labeled as IgG lambda) and BSA was detected by anti-V5 Ab-HRP conjugate. Each point is shown as the mean value of duplicate with standard deviation. Results are demonstrated in FIG. 8.

Competition of MLB and MLD Protein Variants with HIV Envelope Glycoprotein Gp120 for Binding to PGT126 or PGT121 bNAb in ELISA.

The protein variants MLB036, MLB041, MLD033, MLD108 (His6-Myo-Flag) were produced in *E. coli* BL21 and in vivo biotinylated variants MLD068 and MLD049 (His6-Myo-Avi) in *E. coli* BL21 BirA strain. Proteins were purified using Ni-NTA agarose and assayed in ELISA. Increasing concentration of gp120 inhibits binding of the MLB and MLD proteins at a constant concentration μM to bnAb. Their binding to PGT121 or PGT126 bnAb, respectively, was visualized by the anti-Flag M2 Ab-HRP conjugate or in the case of biotinylated protein by streptavidin-HRP. Each point is shown as the mean value of triplicates with standard deviation. Results are presented in FIG. 9.

Immunization of Experimental Mice with a Panel of MLB Variants Induced Serum Antibodies Specifically Recognizing HIV-1 Env.

Mice were immunized by the administration of four doses of individual MLB variants including wild-type (MyoWT). Following immunization, sera were collected and tested in their reactivity with multimerizing HIV-1 gp120 clade B consensus coated on ELISA plates. Antibody titers of IgG isotype were measured in ELISA. Statistical comparison was performed by ANOVA Kruskal-Wallis test with Dunn's post-test (* $P<0.05$). Results are shown in FIG. 10.

Binding of Sera from Mice Immunized with MLB Variants to HIV-1 Multimeric Gp120 is Specifically Inhibited by PGT126.

Sera from mice immunized with MLB036 and MLB041 were tested for reactivity with recombinant multimeric HIV-1 clade B consensus protein coated on ELISA panel in competition with PGT126 as specific inhibitor of MLB or 10E8 (irrelevant mAb control) serially diluted to achieve final concentrations as indicated in blocking buffer was applied with individual MLB036- or MLB041-immunized mouse sera diluted 1:75 after 3rd or 1:200 after 4th immunization. After washing, plates were incubated with rabbit anti-mouse IgG HRP-mAb, developed with a substrate and O.D. 492 nm was measured. 10E8 was applied in control reaction at indicated concentrations. In separate experiment PGT126 at indicated concentration was applied with individual MyoWT-immunized or naive mouse sera diluted 1:200 as the control (MyoWT). Mean values are indicated by horizontal lines. Results are presented in FIG. 11.

The invention claimed is:

1. A polypeptide having a length of up to 180 amino acids and containing a sequence selected from sequences identical or differing at most in 5 amino acids from the sequence:

$$\begin{array}{l}\text{(SEQ ID NO. 2)}\\ \text{KSELAVEILEKGQVRFWMQA}X_{21}X_{22}X_{23}X_{24}\text{GNAKVNY}\\[4pt] \text{IFNEKEIFEGPKYKMHID}X_{50}X_{51}X_{52}\text{GIIEMFMEKLQD}\\[4pt] \text{EDEGTYTFQLQ}X_{76}X_{77}X_{78}X_{79}X_{80}\text{NHSTVVLVGDVFK}\\[4pt] \text{KLQKEAEFQRQEWIRKQG,}\end{array}$$

wherein $X_{21}X_{22}X_{23}X_{24}$ is selected from KAQQ (SEQ ID NO. 33), LSVF (SEQ ID NO. 34), ATPS (SEQ ID NO. 35), EIMW (SEQ ID NO. 36), DGSS (SEQ ID NO. 37), LLPL (SEQ ID NO. 38), WMWW (SEQ ID NO. 39), MNLY (SEQ ID NO. 40), MWRN (SEQ ID NO. 41), IMME (SEQ ID NO. 42), KHQL (SEQ ID NO. 43), HWQF (SEQ ID NO. 44), YAGN (SEQ ID NO. 45) and HGQW (SEQ ID NO. 46);

$X_{50}X_{51}X_{52}$ is selected from RNT, IMF, GHE, PSW, RAN, YFW, ITL, QAM, DMR, WLW, QGE, VQY and VSL;

$X_{76}X_{77}X_{78}X_{79}X_{80}$ is selected from SHHLG (SEQ ID NO. 47), FMLMM (SEQ ID NO. 48), VILIL (SEQ ID NO. 49), IVTPL (SEQ ID NO. 50), DFIIW (SEQ ID NO. 51), MWSE (deletion) (SEQ ID NO. 52), LYYAW (SEQ ID NO. 53), MMIEY (SEQ ID NO. 54), WMTQT (SEQ ID NO. 55), PQLWL (SEQ ID NO. 56), EPIFL (SEQ ID NO. 57) and QTATY (SEQ ID NO. 58);

said polypeptide optionally further having an affinity tag attached to the N-terminus or to the C-terminus of the sequence.

2. The polypeptide according to claim 1, which has the length of up to 180 amino acids and contains a sequence selected from sequences identical or differing at most in 5 amino acids from the sequences:

```
                                      (SEQ ID NO. 3)
KSELAVEILEKGQVRFWMQAKAQQGNAKVNYIFNEKEIFE

GPKYKMHIDIMFGIIEMFMEKLQDEDEGTYTFQLQSHHLG

NHSTVVLVGDVFKKLQKEAEFQRQEWIRKQG
```

```
                                      (SEQ ID NO. 4)
KSELAVEILEKGQVRFWMQALSVFGNAKVNYIFNEKEIFE

GPKYKMHIDRNTGIIEMFMEKLQDEDEGTYTFQLQFMLMM

NHSTVVLVGDVFKKLQKEAEFQRQEWIRKQG
```

```
                                      (SEQ ID NO. 5)
KSELAVEILEKGQVRFWMQAATPSGNAKVNYIFNEKEIFE

GPKYKMHIDGHEGIIEMFMEKLQDEDEGTYTFQLQVILIL

NHSTVVLVGDVFKKLQKEAEFQRQEWIRKQG
```

```
                                      (SEQ ID NO. 6)
KSELAVEILEKGQVRFWMQAEIMWGNAKVNYIFNEKEIFE

GPKYKMHIDPSWGIIEMFMEKLQDEDEGTYTFQLQIVTPL

NHSTVVLVGDVFKKLQKEAEFQRQEWIRKQG
```

```
                                      (SEQ ID NO. 7)
KSELAVEILEKGQVRFWMQADGSSGNAKVNYIFNEKEIFE

GPKYKMHIDRANGIIEMFMEKLQDEDEGTYTFQLQDFIIW

NHSTVVLVGDVFKKLQKEAEFQRQEWIRKQG
```

```
                                      (SEQ ID NO. 8)
KSELAVEILEKGQVRFWMQALLPLGNAKVNYIFNEKEIFE

GPKYKMHIDYFWGIIEMFMEKLQDEDEGTYTFQLQMWSEN

HSTVVLVGDVFKKLQKEAEFQRQEWIRKQG
```

```
                                      (SEQ ID NO. 9)
KSELAVEILEKGQVRFWMQAWMWWGNAKVNYIFNEKEIFE

GPKYKMHIDITLGIIEMFMEKLQDEDEGTYTFQLQLYYAW

NHSTVVLVGDVFKKLQKEAEFQRQEWIRKQG
```

```
                                      (SEQ ID NO. 10)
KSELAVEILEKGQVRFWMQAMNLYGNAKVNYIFNEKEIFE

GPKYKMHIDQAMGIIEMFMEKLQDEDEGTYTFQLQMMIEY

NHSTVVLVGDVFKKLQKEAEFQRQEWIRKQG
```

```
                                      (SEQ ID NO. 11)
KSELAVEILEKGQVRFWMQAMWRNGNAKVNYIFNEKEIFE

GPKYKMHIDRNTGIIEMFMEKLQDEDEGTYTFQLQWMTQT

NHSTVVLVGDVFKKLQKEAEFQRQEWIRKQG
```

```
                                      (SEQ ID NO. 12)
KSELAVEILEKGQVRFWMQAIMMEGNAKVNYIFNEKEIFE

GPKYKMHIDDMRGIIEMFMEKLQDEDEGTYTFQLQIVTPL

NHSTVVLVGDVFKKLQKEAEFQRQEWIRKQG
```

-continued
```
                                      (SEQ ID NO. 13)
KSELAVEILEKGQVRFWMQAKHQLGNAKVNYIFNEKEIFE

GPKYKMHIDWLWGIIEMFMEKLQDEDEGTYTFQLQIVTPL

NHSTVVLVGDVFKKLQKEAEFQRQEWIRKQG
```

```
                                      (SEQ ID NO. 14)
KSELAVEILEKGQVRFWMQAHWQFGNAKVNYIFNEKEIFE

GPKYKMHIDQGEGIIEMFMEKLQDEDEGTYTFQLQPQLWL

NHSTVVLVGDVFKKLQKEAEFQRQEWIRKQG
```

```
                                      (SEQ ID NO. 15)
KSELAVEILEKGQVRFWMQAYAGNGNAKVNYIFNEKEIFE

GPKYKMHIDVQYGIIEMFMEKLQDEDEGTYTFQLQEPIFL

NHSTVVLVGDVFKKLQKEAEFQRQEWIRKQG
and
                                      (SEQ ID NO. 16)
KSELAVEILEKGQVRFWMQAHGQWGNAKVNYIFNEKEIFE

GPKYKMHIDVSLGIIEMFMEKLQDEDEGTYTFQLQQTATY

NHSTVVLVGDVFKKLQKEAEFQRQEWIRKQG,
``` said polypeptide optionally further having an affinity tag attached to the N-terminus or to the C-terminus of the sequence.

3. The polypeptide according to claim 1, having the following variables in SEQ ID NO. 2:

$X_{21}X_{22}X_{23}X_{24}$ is selected from KAQQ (SEQ ID NO. 33), LSVF (SEQ ID NO. 34), ATPS (SEQ ID NO. 35), EIMW (SEQ ID NO. 36), DGSS (SEQ ID NO. 37), LLPL (SEQ ID NO. 38), WMWW (SEQ ID NO. 39), and MNLY (SEQ ID NO. 40);

$X_{50}X_{51}X_{52}$ is selected from RNT, IMF, GHE, PSW, RAN, YFW, ITL and QAM;

$X_{76}X_{77}X_{78}X_{79}X_{80}$ is selected from SHHLG (SEQ ID NO. 47), FMLMM (SEQ ID NO. 48), VILIL (SEQ ID NO. 49), IVTPL (SEQ ID NO. 50), DFIIW (SEQ ID NO. 51), MWSE (deletion) (SEQ ID NO. 52), LYYAW (SEQ ID NO. 53) and MMIEY (SEQ ID NO. 54).

4. The polypeptide according to claim 1, having the following variables in SEQ ID NO. 2:

$X_{21}X_{22}X_{23}X_{24}$ is selected from MWRN (SEQ ID NO. 41), IMME (SEQ ID NO. 42) and KHQL (SEQ ID NO. 43);

$X_{50}X_{51}X_{52}$ is selected from RNT, DMR and WLW;

$X_{76}X_{77}X_{78}X_{79}X_{80}$ is selected from IVTPL (SEQ ID NO. 50) and WMTQT (SEQ ID NO. 55).

5. The polypeptide according to claim 1, having the following variables in SEQ ID NO. 2:

$X_{21}X_{22}X_{23}X_{24}$ is selected from HWQF (SEQ ID NO. 44), YAGN (SEQ ID NO. 45) and HGQW (SEQ ID NO. 46);

$X_{50}X_{51}X_{52}$ is selected from QGE, VQY and VSL;

$X_{76}X_{77}X_{78}X_{79}X_{80}$ is selected from PQLWL (SEQ ID NO. 56), EPIFL (SEQ ID NO. 57) and QTATY (SEQ ID NO. 58).

6. The polypeptide according to claim 1, which has the length of up to 160 amino acids.

7. A conjugate of the polypeptide according to claim 1 with serum albumin or with heat shock protein hsp70.

8. The polypeptide according to claim 1 for induction of HIV-1 virus-neutralizing antibodies in a subject in need thereof.

9. The polypeptide according to claim 3 for induction of HIV-1 virus-neutralizing antibodies targeting the epitope targeted by broadly neutralizing antibody 10E8 in a subject in need thereof.

10. The polypeptide according to claim 4 for induction of HIV-1 virus-neutralizing antibodies targeting the epitope targeted by broadly neutralizing antibody PGT126 in a subject in need thereof.

11. The polypeptide according to claim 5 for induction of HIV-1 virus-neutralizing antibodies targeting the epitope targeted by broadly neutralizing antibody PGT121 in a subject in need thereof.

12. A complementary DNA sequence coding for the amino acid sequence of the polypeptide according to claim 1.

13. A host cell, characterized in that it contains at least one DNA sequence of claim 12.

14. The conjugate according to claim 7 for induction of HIV-1 virus-neutralizing antibodies in a subject in need thereof.

15. The conjugate according to claim 7 for prevention of diseases or disorders caused by HIV-1 virus.

16. The polypeptide according to claim 1, which has the length of up to 140 amino acids.

17. The polypeptide according to claim 1, which has the length of up to 120 amino acids.

* * * * *

SEQUENCE LISTING

<160> NUMBER OF SEQ ID NOS: 60

<210> SEQ ID NO 1
<211> LENGTH: 111
<212> TYPE: PRT
<213> ORGANISM: homo sapiens

<400> SEQUENCE: 1

Lys Ser Glu Leu Ala Val Glu Ile Leu Glu Lys Gly Gln Val Arg Phe
1               5                   10                  15

Trp Met Gln Ala Glu Lys Leu Ser Gly Asn Ala Lys Val Asn Tyr Ile
            20                  25                  30

Phe Asn Glu Lys Glu Ile Phe Glu Gly Pro Lys Tyr Lys Met His Ile
        35                  40                  45

Asp Arg Asn Thr Gly Ile Ile Glu Met Phe Met Glu Lys Leu Gln Asp
    50                  55                  60

Glu Asp Glu Gly Thr Tyr Thr Phe Gln Leu Gln Asp Gly Lys Ala Thr
65                  70                  75                  80

Asn His Ser Thr Val Val Leu Val Gly Asp Val Phe Lys Lys Leu Gln
                85                  90                  95

Lys Glu Ala Glu Phe Gln Arg Gln Glu Trp Ile Arg Lys Gln Gly
            100                 105                 110

<210> SEQ ID NO 2
<211> LENGTH: 111
<212> TYPE: PRT
<213> ORGANISM: artificial
<220> FEATURE:
<223> OTHER INFORMATION: mutated myomesin-1 domain 10 protein
<220> FEATURE:
<221> NAME/KEY: VARIANT
<222> LOCATION: (21)..(24)
<223> OTHER INFORMATION: KAQQ, LSVF, ATPS, EIMW, DGSS, LLPL, WMWW, MNLY,
      MWRN, IMME, KHQL, HWQF, YAGN, or HGQW
<220> FEATURE:
<221> NAME/KEY: VARIANT
<222> LOCATION: (50)..(52)
<223> OTHER INFORMATION: RNT, IMF, GHE, PSW, RAN, YFW, ITL, QAM, DMR,
      WLW, QGE, VQY, or VSL
<220> FEATURE:
<221> NAME/KEY: VARIANT
<222> LOCATION: (76)..(80)
<223> OTHER INFORMATION: SHHLG, FMLMM, VILIL, IVTPL, DFIIW,
      MWSE(deletion), LYYAW, MMIEY, WMTQT, PQLWL, EPIFL, or QTATY

<400> SEQUENCE: 2

Lys Ser Glu Leu Ala Val Glu Ile Leu Glu Lys Gly Gln Val Arg Phe
1               5                   10                  15

Trp Met Gln Ala Xaa Xaa Xaa Xaa Gly Asn Ala Lys Val Asn Tyr Ile
            20                  25                  30

Phe Asn Glu Lys Glu Ile Phe Glu Gly Pro Lys Tyr Lys Met His Ile
        35                  40                  45

Asp Xaa Xaa Xaa Gly Ile Ile Glu Met Phe Met Glu Lys Leu Gln Asp
    50                  55                  60

Glu Asp Glu Gly Thr Tyr Thr Phe Gln Leu Gln Xaa Xaa Xaa Xaa Xaa
65                  70                  75                  80

Asn His Ser Thr Val Val Leu Val Gly Asp Val Phe Lys Lys Leu Gln
                85                  90                  95

Lys Glu Ala Glu Phe Gln Arg Gln Glu Trp Ile Arg Lys Gln Gly
            100                 105                 110

<210> SEQ ID NO 3

-continued

```
<211> LENGTH: 111
<212> TYPE: PRT
<213> ORGANISM: artificial
<220> FEATURE:
<223> OTHER INFORMATION: mutated myomesin-1 domain 10 protein

<400> SEQUENCE: 3

Lys Ser Glu Leu Ala Val Glu Ile Leu Glu Lys Gly Gln Val Arg Phe
1               5                   10                  15

Trp Met Gln Ala Lys Ala Gln Gln Gly Asn Ala Lys Val Asn Tyr Ile
                20                  25                  30

Phe Asn Glu Lys Glu Ile Phe Glu Gly Pro Lys Tyr Lys Met His Ile
            35                  40                  45

Asp Ile Met Phe Gly Ile Ile Glu Met Phe Met Glu Lys Leu Gln Asp
        50                  55                  60

Glu Asp Glu Gly Thr Tyr Thr Phe Gln Leu Gln Ser His His Leu Gly
65                  70                  75                  80

Asn His Ser Thr Val Val Leu Val Gly Asp Val Phe Lys Lys Leu Gln
                85                  90                  95

Lys Glu Ala Glu Phe Gln Arg Gln Glu Trp Ile Arg Lys Gln Gly
            100                 105                 110

<210> SEQ ID NO 4
<211> LENGTH: 111
<212> TYPE: PRT
<213> ORGANISM: artificial
<220> FEATURE:
<223> OTHER INFORMATION: mutated myomesin-1 domain 10 protein

<400> SEQUENCE: 4

Lys Ser Glu Leu Ala Val Glu Ile Leu Glu Lys Gly Gln Val Arg Phe
1               5                   10                  15

Trp Met Gln Ala Leu Ser Val Phe Gly Asn Ala Lys Val Asn Tyr Ile
                20                  25                  30

Phe Asn Glu Lys Glu Ile Phe Glu Gly Pro Lys Tyr Lys Met His Ile
            35                  40                  45

Asp Arg Asn Thr Gly Ile Ile Glu Met Phe Met Glu Lys Leu Gln Asp
        50                  55                  60

Glu Asp Glu Gly Thr Tyr Thr Phe Gln Leu Gln Phe Met Leu Met Met
65                  70                  75                  80

Asn His Ser Thr Val Val Leu Val Gly Asp Val Phe Lys Lys Leu Gln
                85                  90                  95

Lys Glu Ala Glu Phe Gln Arg Gln Glu Trp Ile Arg Lys Gln Gly
            100                 105                 110

<210> SEQ ID NO 5
<211> LENGTH: 111
<212> TYPE: PRT
<213> ORGANISM: artificial
<220> FEATURE:
<223> OTHER INFORMATION: mutated myomesin-1 domain 10 protein

<400> SEQUENCE: 5

Lys Ser Glu Leu Ala Val Glu Ile Leu Glu Lys Gly Gln Val Arg Phe
1               5                   10                  15

Trp Met Gln Ala Ala Thr Pro Ser Gly Asn Ala Lys Val Asn Tyr Ile
                20                  25                  30

Phe Asn Glu Lys Glu Ile Phe Glu Gly Pro Lys Tyr Lys Met His Ile
            35                  40                  45
```

```
Asp Gly His Glu Gly Ile Ile Glu Met Phe Met Glu Lys Leu Gln Asp
    50              55              60

Glu Asp Glu Gly Thr Tyr Thr Phe Gln Leu Gln Val Ile Leu Ile Leu
65              70              75              80

Asn His Ser Thr Val Val Leu Val Gly Asp Val Phe Lys Lys Leu Gln
                85              90              95

Lys Glu Ala Glu Phe Gln Arg Gln Glu Trp Ile Arg Lys Gln Gly
            100             105             110

<210> SEQ ID NO 6
<211> LENGTH: 111
<212> TYPE: PRT
<213> ORGANISM: artificial
<220> FEATURE:
<223> OTHER INFORMATION: mutated myomesin-1 domain 10 protein

<400> SEQUENCE: 6

Lys Ser Glu Leu Ala Val Glu Ile Leu Glu Lys Gly Gln Val Arg Phe
1               5               10              15

Trp Met Gln Ala Glu Ile Met Trp Gly Asn Ala Lys Val Asn Tyr Ile
            20              25              30

Phe Asn Glu Lys Glu Ile Phe Glu Gly Pro Lys Tyr Lys Met His Ile
        35              40              45

Asp Pro Ser Trp Gly Ile Ile Glu Met Phe Met Glu Lys Leu Gln Asp
    50              55              60

Glu Asp Glu Gly Thr Tyr Thr Phe Gln Leu Gln Ile Val Thr Pro Leu
65              70              75              80

Asn His Ser Thr Val Val Leu Val Gly Asp Val Phe Lys Lys Leu Gln
                85              90              95

Lys Glu Ala Glu Phe Gln Arg Gln Glu Trp Ile Arg Lys Gln Gly
            100             105             110

<210> SEQ ID NO 7
<211> LENGTH: 111
<212> TYPE: PRT
<213> ORGANISM: artificial
<220> FEATURE:
<223> OTHER INFORMATION: mutated myomesin-1 domain 10 protein

<400> SEQUENCE: 7

Lys Ser Glu Leu Ala Val Glu Ile Leu Glu Lys Gly Gln Val Arg Phe
1               5               10              15

Trp Met Gln Ala Asp Gly Ser Ser Gly Asn Ala Lys Val Asn Tyr Ile
            20              25              30

Phe Asn Glu Lys Glu Ile Phe Glu Gly Pro Lys Tyr Lys Met His Ile
        35              40              45

Asp Arg Ala Asn Gly Ile Ile Glu Met Phe Met Glu Lys Leu Gln Asp
    50              55              60

Glu Asp Glu Gly Thr Tyr Thr Phe Gln Leu Gln Asp Phe Ile Ile Trp
65              70              75              80

Asn His Ser Thr Val Val Leu Val Gly Asp Val Phe Lys Lys Leu Gln
                85              90              95

Lys Glu Ala Glu Phe Gln Arg Gln Glu Trp Ile Arg Lys Gln Gly
            100             105             110

<210> SEQ ID NO 8
<211> LENGTH: 110
<212> TYPE: PRT
<213> ORGANISM: artificial
```

-continued

```
<220> FEATURE:
<223> OTHER INFORMATION: mutated myomesin-1 domain 10 protein

<400> SEQUENCE: 8

Lys Ser Glu Leu Ala Val Glu Ile Leu Glu Lys Gly Gln Val Arg Phe
1               5                   10                  15

Trp Met Gln Ala Leu Leu Pro Leu Gly Asn Ala Lys Val Asn Tyr Ile
            20                  25                  30

Phe Asn Glu Lys Glu Ile Phe Glu Gly Pro Lys Tyr Lys Met His Ile
        35                  40                  45

Asp Tyr Phe Trp Gly Ile Ile Glu Met Phe Met Glu Lys Leu Gln Asp
    50                  55                  60

Glu Asp Glu Gly Thr Tyr Thr Phe Gln Leu Gln Met Trp Ser Glu Asn
65                  70                  75                  80

His Ser Thr Val Val Leu Val Gly Asp Val Phe Lys Lys Leu Gln Lys
                85                  90                  95

Glu Ala Glu Phe Gln Arg Gln Glu Trp Ile Arg Lys Gln Gly
            100                 105                 110

<210> SEQ ID NO 9
<211> LENGTH: 111
<212> TYPE: PRT
<213> ORGANISM: artificial
<220> FEATURE:
<223> OTHER INFORMATION: mutated myomesin-1 domain 10 protein

<400> SEQUENCE: 9

Lys Ser Glu Leu Ala Val Glu Ile Leu Glu Lys Gly Gln Val Arg Phe
1               5                   10                  15

Trp Met Gln Ala Trp Met Trp Trp Gly Asn Ala Lys Val Asn Tyr Ile
            20                  25                  30

Phe Asn Glu Lys Glu Ile Phe Glu Gly Pro Lys Tyr Lys Met His Ile
        35                  40                  45

Asp Ile Thr Leu Gly Ile Ile Glu Met Phe Met Glu Lys Leu Gln Asp
    50                  55                  60

Glu Asp Glu Gly Thr Tyr Thr Phe Gln Leu Gln Leu Tyr Tyr Ala Trp
65                  70                  75                  80

Asn His Ser Thr Val Val Leu Val Gly Asp Val Phe Lys Lys Leu Gln
                85                  90                  95

Lys Glu Ala Glu Phe Gln Arg Gln Glu Trp Ile Arg Lys Gln Gly
            100                 105                 110

<210> SEQ ID NO 10
<211> LENGTH: 111
<212> TYPE: PRT
<213> ORGANISM: artificial
<220> FEATURE:
<223> OTHER INFORMATION: mutated myomesin-1 domain 10 protein

<400> SEQUENCE: 10

Lys Ser Glu Leu Ala Val Glu Ile Leu Glu Lys Gly Gln Val Arg Phe
1               5                   10                  15

Trp Met Gln Ala Met Asn Leu Tyr Gly Asn Ala Lys Val Asn Tyr Ile
            20                  25                  30

Phe Asn Glu Lys Glu Ile Phe Glu Gly Pro Lys Tyr Lys Met His Ile
        35                  40                  45

Asp Gln Ala Met Gly Ile Ile Glu Met Phe Met Glu Lys Leu Gln Asp
    50                  55                  60
```

```
Glu Asp Glu Gly Thr Tyr Thr Phe Gln Leu Gln Met Met Ile Glu Tyr
65              70              75              80

Asn His Ser Thr Val Val Leu Val Gly Asp Val Phe Lys Lys Leu Gln
            85              90              95

Lys Glu Ala Glu Phe Gln Arg Gln Glu Trp Ile Arg Lys Gln Gly
        100             105             110

<210> SEQ ID NO 11
<211> LENGTH: 111
<212> TYPE: PRT
<213> ORGANISM: artificial
<220> FEATURE:
<223> OTHER INFORMATION: mutated myomesin-1 domain 10 protein

<400> SEQUENCE: 11

Lys Ser Glu Leu Ala Val Glu Ile Leu Glu Lys Gly Gln Val Arg Phe
1               5               10              15

Trp Met Gln Ala Met Trp Arg Asn Gly Asn Ala Lys Val Asn Tyr Ile
            20              25              30

Phe Asn Glu Lys Glu Ile Phe Glu Gly Pro Lys Tyr Lys Met His Ile
        35              40              45

Asp Arg Asn Thr Gly Ile Ile Glu Met Phe Met Glu Lys Leu Gln Asp
    50              55              60

Glu Asp Glu Gly Thr Tyr Thr Phe Gln Leu Gln Trp Met Thr Gln Thr
65              70              75              80

Asn His Ser Thr Val Val Leu Val Gly Asp Val Phe Lys Lys Leu Gln
            85              90              95

Lys Glu Ala Glu Phe Gln Arg Gln Glu Trp Ile Arg Lys Gln Gly
        100             105             110

<210> SEQ ID NO 12
<211> LENGTH: 111
<212> TYPE: PRT
<213> ORGANISM: artificial
<220> FEATURE:
<223> OTHER INFORMATION: mutated myomesin-1 domain 10 protein

<400> SEQUENCE: 12

Lys Ser Glu Leu Ala Val Glu Ile Leu Glu Lys Gly Gln Val Arg Phe
1               5               10              15

Trp Met Gln Ala Ile Met Met Glu Gly Asn Ala Lys Val Asn Tyr Ile
            20              25              30

Phe Asn Glu Lys Glu Ile Phe Glu Gly Pro Lys Tyr Lys Met His Ile
        35              40              45

Asp Asp Met Arg Gly Ile Ile Glu Met Phe Met Glu Lys Leu Gln Asp
    50              55              60

Glu Asp Glu Gly Thr Tyr Thr Phe Gln Leu Gln Ile Val Thr Pro Leu
65              70              75              80

Asn His Ser Thr Val Val Leu Val Gly Asp Val Phe Lys Lys Leu Gln
            85              90              95

Lys Glu Ala Glu Phe Gln Arg Gln Glu Trp Ile Arg Lys Gln Gly
        100             105             110

<210> SEQ ID NO 13
<211> LENGTH: 111
<212> TYPE: PRT
<213> ORGANISM: artificial
<220> FEATURE:
<223> OTHER INFORMATION: mutated myomesin-1 domain 10 protein
```

<400> SEQUENCE: 13

```
Lys Ser Glu Leu Ala Val Glu Ile Leu Glu Lys Gly Gln Val Arg Phe
1               5                   10                  15

Trp Met Gln Ala Lys His Gln Leu Gly Asn Ala Lys Val Asn Tyr Ile
            20                  25                  30

Phe Asn Glu Lys Glu Ile Phe Glu Gly Pro Lys Tyr Lys Met His Ile
            35                  40                  45

Asp Trp Leu Trp Gly Ile Ile Glu Met Phe Met Glu Lys Leu Gln Asp
        50                  55                  60

Glu Asp Glu Gly Thr Tyr Thr Phe Gln Leu Gln Ile Val Thr Pro Leu
65                  70                  75                  80

Asn His Ser Thr Val Val Leu Val Gly Asp Val Phe Lys Lys Leu Gln
                85                  90                  95

Lys Glu Ala Glu Phe Gln Arg Gln Glu Trp Ile Arg Lys Gln Gly
            100                 105                 110
```

<210> SEQ ID NO 14
<211> LENGTH: 111
<212> TYPE: PRT
<213> ORGANISM: artificial
<220> FEATURE:
<223> OTHER INFORMATION: mutated myomesin-1 domain 10 protein

<400> SEQUENCE: 14

```
Lys Ser Glu Leu Ala Val Glu Ile Leu Glu Lys Gly Gln Val Arg Phe
1               5                   10                  15

Trp Met Gln Ala His Trp Gln Phe Gly Asn Ala Lys Val Asn Tyr Ile
            20                  25                  30

Phe Asn Glu Lys Glu Ile Phe Glu Gly Pro Lys Tyr Lys Met His Ile
            35                  40                  45

Asp Gln Gly Glu Gly Ile Ile Glu Met Phe Met Glu Lys Leu Gln Asp
        50                  55                  60

Glu Asp Glu Gly Thr Tyr Thr Phe Gln Leu Gln Pro Gln Leu Trp Leu
65                  70                  75                  80

Asn His Ser Thr Val Val Leu Val Gly Asp Val Phe Lys Lys Leu Gln
                85                  90                  95

Lys Glu Ala Glu Phe Gln Arg Gln Glu Trp Ile Arg Lys Gln Gly
            100                 105                 110
```

<210> SEQ ID NO 15
<211> LENGTH: 111
<212> TYPE: PRT
<213> ORGANISM: artificial
<220> FEATURE:
<223> OTHER INFORMATION: mutated myomesin-1 domain 10 protein

<400> SEQUENCE: 15

```
Lys Ser Glu Leu Ala Val Glu Ile Leu Glu Lys Gly Gln Val Arg Phe
1               5                   10                  15

Trp Met Gln Ala Tyr Ala Gly Asn Gly Asn Ala Lys Val Asn Tyr Ile
            20                  25                  30

Phe Asn Glu Lys Glu Ile Phe Glu Gly Pro Lys Tyr Lys Met His Ile
            35                  40                  45

Asp Val Gln Tyr Gly Ile Ile Glu Met Phe Met Glu Lys Leu Gln Asp
        50                  55                  60

Glu Asp Glu Gly Thr Tyr Thr Phe Gln Leu Gln Glu Pro Ile Phe Leu
65                  70                  75                  80
```

```
Asn His Ser Thr Val Val Leu Val Gly Asp Val Phe Lys Lys Leu Gln
                85                  90                  95

Lys Glu Ala Glu Phe Gln Arg Gln Glu Trp Ile Arg Lys Gln Gly
        100                 105                 110

<210> SEQ ID NO 16
<211> LENGTH: 111
<212> TYPE: PRT
<213> ORGANISM: artificial
<220> FEATURE:
<223> OTHER INFORMATION: mutated myomesin-1 domain 10 protein

<400> SEQUENCE: 16

Lys Ser Glu Leu Ala Val Glu Ile Leu Glu Lys Gly Gln Val Arg Phe
1               5                   10                  15

Trp Met Gln Ala His Gly Gln Trp Gly Asn Ala Lys Val Asn Tyr Ile
            20                  25                  30

Phe Asn Glu Lys Glu Ile Phe Glu Gly Pro Lys Tyr Lys Met His Ile
        35                  40                  45

Asp Val Ser Leu Gly Ile Ile Glu Met Phe Met Glu Lys Leu Gln Asp
    50                  55                  60

Glu Asp Glu Gly Thr Tyr Thr Phe Gln Leu Gln Gln Thr Ala Thr Tyr
65                  70                  75                  80

Asn His Ser Thr Val Val Leu Val Gly Asp Val Phe Lys Lys Leu Gln
                85                  90                  95

Lys Glu Ala Glu Phe Gln Arg Gln Glu Trp Ile Arg Lys Gln Gly
        100                 105                 110

<210> SEQ ID NO 17
<211> LENGTH: 29
<212> TYPE: DNA
<213> ORGANISM: artificial
<220> FEATURE:
<223> OTHER INFORMATION: Myom10-F

<400> SEQUENCE: 17
catatgaaat cagagttggc agttgaaat                                      29

<210> SEQ ID NO 18
<211> LENGTH: 33
<212> TYPE: DNA
<213> ORGANISM: artificial
<220> FEATURE:
<223> OTHER INFORMATION: Myom10-R

<400> SEQUENCE: 18
caagaatgga tcaggaaaca aggttaagga tcc                                 33

<210> SEQ ID NO 19
<211> LENGTH: 70
<212> TYPE: DNA
<213> ORGANISM: artificial
<220> FEATURE:
<223> OTHER INFORMATION: Myom-LP-n1F

<400> SEQUENCE: 19
aatgccaaag tgaactatat cttcaacgag aaagaaatct tcgaaggtcc gaaatacaaa    60
atgcatattg                                                          70

<210> SEQ ID NO 20
<211> LENGTH: 58
<212> TYPE: DNA
```

-continued

```
<213> ORGANISM: artificial
<220> FEATURE:
<223> OTHER INFORMATION: Myom-LP_2F
<220> FEATURE:
<221> NAME/KEY: misc_feature
<222> LOCATION: (28)..(36)
<223> OTHER INFORMATION: randomized positions

<400> SEQUENCE: 20
ggtccgaaat acaaaatgca tattgatnnn nnnnnnggca tcatcgaaat gtttatgg          58

<210> SEQ ID NO 21
<211> LENGTH: 66
<212> TYPE: DNA
<213> ORGANISM: artificial
<220> FEATURE:
<223> OTHER INFORMATION: Myom-LP_n2R

<400> SEQUENCE: 21
cagctgaaag gtataggtgc cttcatcttc atcctgcagt ttttccataa acatttcgat        60
gatgcc                                                                   66

<210> SEQ ID NO 22
<211> LENGTH: 58
<212> TYPE: DNA
<213> ORGANISM: artificial
<220> FEATURE:
<223> OTHER INFORMATION: Myom-LP_1F
<220> FEATURE:
<221> NAME/KEY: misc_feature
<222> LOCATION: (20)..(31)
<223> OTHER INFORMATION: randomized positions

<400> SEQUENCE: 22 tcgttttgg atgcaggcan nnnnnnnnnn nggtaatgcc aaagtgaact atatcttc           58

<210> SEQ ID NO 23
<211> LENGTH: 60
<212> TYPE: DNA
<213> ORGANISM: artificial
<220> FEATURE:
<223> OTHER INFORMATION: Myom-LP_3R
<220> FEATURE:
<221> NAME/KEY: misc_feature
<222> LOCATION: (23)..(37)
<223> OTHER INFORMATION: randomized positions

<400> SEQUENCE: 23
ccagaacaac ggttgaatga ttnnnnnnnn nnnnnnnctg cagctgaaag gtataggtgc        60

<210> SEQ ID NO 24
<211> LENGTH: 60
<212> TYPE: DNA
<213> ORGANISM: artificial
<220> FEATURE:
<223> OTHER INFORMATION: L-for

<400> SEQUENCE: 24
aaaagcgagc tggccgtgga aattctggaa aaaggtcagg ttcgttttg gatgcaggca         60

<210> SEQ ID NO 25
<211> LENGTH: 93
<212> TYPE: DNA
<213> ORGANISM: artificial
<220> FEATURE:
<223> OTHER INFORMATION: L-rev

<400> SEQUENCE: 25
```

-continued

```
accctgttta cgaatccatt cttggcgctg aaattctgct tcttttttgca gttttttgaa        60 cacgtcacca accagaacaa cggttgaatg att                                      93

<210> SEQ ID NO 26
<211> LENGTH: 87
<212> TYPE: DNA
<213> ORGANISM: artificial
<220> FEATURE:
<223> OTHER INFORMATION: JOIN-F

<400> SEQUENCE: 26
ctatagggag accacaacgg tttccctcta gaaataattt tgtttaactt taagaaggag        60
atatacatat gaaaagcgag ctggccg                                            87

<210> SEQ ID NO 27
<211> LENGTH: 40
<212> TYPE: DNA
<213> ORGANISM: artificial
<220> FEATURE:
<223> OTHER INFORMATION: JOIN-R

<400> SEQUENCE: 27
gaaccgaccg cggatccacc ctgtttacga atccattctt                              40

<210> SEQ ID NO 28
<211> LENGTH: 41
<212> TYPE: DNA
<213> ORGANISM: artificial
<220> FEATURE:
<223> OTHER INFORMATION: T7B

<400> SEQUENCE: 28
atacgaaatt aatacgactc actatanggga gaccacaacg g                           41

<210> SEQ ID NO 29
<211> LENGTH: 45
<212> TYPE: DNA
<213> ORGANISM: artificial
<220> FEATURE:
<223> OTHER INFORMATION: TolAk

<400> SEQUENCE: 29
ccgcacacca gtaaggtgtg cggtttcagt tgccgctttc tttct                        45

<210> SEQ ID NO 30
<211> LENGTH: 19
<212> TYPE: DNA
<213> ORGANISM: artificial
<220> FEATURE:
<223> OTHER INFORMATION: P7 link

<400> SEQUENCE: 30
ggatccgcgg tcggttcga                                                     19

<210> SEQ ID NO 31
<211> LENGTH: 36
<212> TYPE: DNA
<213> ORGANISM: artificial
<220> FEATURE:
<223> OTHER INFORMATION: TolA rev

<400> SEQUENCE: 31
tttccgctcg agctacggtt tgaagtccaa tggcgc                                  36
```

```
<210> SEQ ID NO 32
<211> LENGTH: 61
<212> TYPE: DNA
<213> ORGANISM: artificial
<220> FEATURE:
<223> OTHER INFORMATION: His-Myo-F

<400> SEQUENCE: 32
cagtccatgg gcagcagcca tcatcatcat catcacagca gcggcaaaag cgagctggcc        60
g                                                                        61

<210> SEQ ID NO 33
<211> LENGTH: 4
<212> TYPE: PRT
<213> ORGANISM: artificial
<220> FEATURE:
<223> OTHER INFORMATION: part of SEQ ID NO. 2

<400> SEQUENCE: 33

Lys Ala Gln Gln
1

<210> SEQ ID NO 34
<211> LENGTH: 4
<212> TYPE: PRT
<213> ORGANISM: artificial
<220> FEATURE:
<223> OTHER INFORMATION: part of SEQ ID NO. 2

<400> SEQUENCE: 34

Leu Ser Val Phe
1

<210> SEQ ID NO 35
<211> LENGTH: 4
<212> TYPE: PRT
<213> ORGANISM: artificial
<220> FEATURE:
<223> OTHER INFORMATION: part of SEQ ID NO. 2

<400> SEQUENCE: 35

Ala Thr Pro Ser
1

<210> SEQ ID NO 36
<211> LENGTH: 4
<212> TYPE: PRT
<213> ORGANISM: artificial
<220> FEATURE:
<223> OTHER INFORMATION: part of SEQ ID NO. 2

<400> SEQUENCE: 36

Glu Ile Met Trp
1

<210> SEQ ID NO 37
<211> LENGTH: 4
<212> TYPE: PRT
<213> ORGANISM: artificial
<220> FEATURE:
<223> OTHER INFORMATION: part of SEQ ID NO. 2

<400> SEQUENCE: 37

Asp Gly Ser Ser
1
```

```
<210> SEQ ID NO 38
<211> LENGTH: 4
<212> TYPE: PRT
<213> ORGANISM: artificial
<220> FEATURE:
<223> OTHER INFORMATION: part of SEQ ID NO. 2

<400> SEQUENCE: 38

Leu Leu Pro Leu
1

<210> SEQ ID NO 39
<211> LENGTH: 4
<212> TYPE: PRT
<213> ORGANISM: artificial
<220> FEATURE:
<223> OTHER INFORMATION: part of SEQ ID NO. 2

<400> SEQUENCE: 39

Trp Met Trp Trp
1

<210> SEQ ID NO 40
<211> LENGTH: 4
<212> TYPE: PRT
<213> ORGANISM: artificial
<220> FEATURE:
<223> OTHER INFORMATION: part of SEQ ID NO. 2

<400> SEQUENCE: 40

Met Asn Leu Tyr
1

<210> SEQ ID NO 41
<211> LENGTH: 4
<212> TYPE: PRT
<213> ORGANISM: artificial
<220> FEATURE:
<223> OTHER INFORMATION: part of SEQ ID NO. 2

<400> SEQUENCE: 41

Met Trp Arg Asn
1

<210> SEQ ID NO 42
<211> LENGTH: 4
<212> TYPE: PRT
<213> ORGANISM: artificial
<220> FEATURE:
<223> OTHER INFORMATION: part of SEQ ID NO. 2

<400> SEQUENCE: 42

Ile Met Met Glu
1

<210> SEQ ID NO 43
<211> LENGTH: 4
<212> TYPE: PRT
<213> ORGANISM: artificial
<220> FEATURE:
<223> OTHER INFORMATION: part of SEQ ID NO. 2

<400> SEQUENCE: 43

Lys His Gln Leu
1
```

-continued

```
<210> SEQ ID NO 44
<211> LENGTH: 4
<212> TYPE: PRT
<213> ORGANISM: artificial
<220> FEATURE:
<223> OTHER INFORMATION: part of SEQ ID NO. 2

<400> SEQUENCE: 44

His Trp Gln Phe
1

<210> SEQ ID NO 45
<211> LENGTH: 4
<212> TYPE: PRT
<213> ORGANISM: artificial
<220> FEATURE:
<223> OTHER INFORMATION: part of SEQ ID NO. 2

<400> SEQUENCE: 45

Tyr Ala Gly Asn
1

<210> SEQ ID NO 46
<211> LENGTH: 4
<212> TYPE: PRT
<213> ORGANISM: artificial
<220> FEATURE:
<223> OTHER INFORMATION: part of SEQ ID NO. 2

<400> SEQUENCE: 46

His Gly Gln Trp
1

<210> SEQ ID NO 47
<211> LENGTH: 5
<212> TYPE: PRT
<213> ORGANISM: artificial
<220> FEATURE:
<223> OTHER INFORMATION: part of SEQ ID NO. 2

<400> SEQUENCE: 47

Ser His His Leu Gly
1               5

<210> SEQ ID NO 48
<211> LENGTH: 5
<212> TYPE: PRT
<213> ORGANISM: artificial
<220> FEATURE:
<223> OTHER INFORMATION: part of SEQ ID NO. 2

<400> SEQUENCE: 48

Phe Met Leu Met Met
1               5

<210> SEQ ID NO 49
<211> LENGTH: 5
<212> TYPE: PRT
<213> ORGANISM: artificial
<220> FEATURE:
<223> OTHER INFORMATION: part of SEQ ID NO. 2

<400> SEQUENCE: 49

Val Ile Leu Ile Leu
1               5

<210> SEQ ID NO 50
```

```
<211> LENGTH: 5
<212> TYPE: PRT
<213> ORGANISM: artificial
<220> FEATURE:
<223> OTHER INFORMATION: part of SEQ ID NO. 2

<400> SEQUENCE: 50

Ile Val Thr Pro Leu
1               5

<210> SEQ ID NO 51
<211> LENGTH: 5
<212> TYPE: PRT
<213> ORGANISM: artificial
<220> FEATURE:
<223> OTHER INFORMATION: part of SEQ ID NO. 2

<400> SEQUENCE: 51

Asp Phe Ile Ile Trp
1               5

<210> SEQ ID NO 52
<211> LENGTH: 4
<212> TYPE: PRT
<213> ORGANISM: artificial
<220> FEATURE:
<223> OTHER INFORMATION: part of SEQ ID NO. 2

<400> SEQUENCE: 52

Met Trp Ser Glu
1

<210> SEQ ID NO 53
<211> LENGTH: 5
<212> TYPE: PRT
<213> ORGANISM: artificial
<220> FEATURE:
<223> OTHER INFORMATION: part of SEQ ID NO. 2

<400> SEQUENCE: 53

Leu Tyr Tyr Ala Trp
1               5

<210> SEQ ID NO 54
<211> LENGTH: 5
<212> TYPE: PRT
<213> ORGANISM: artificial
<220> FEATURE:
<223> OTHER INFORMATION: part of SEQ ID NO. 2

<400> SEQUENCE: 54

Met Met Ile Glu Tyr
1               5

<210> SEQ ID NO 55
<211> LENGTH: 5
<212> TYPE: PRT
<213> ORGANISM: artificial
<220> FEATURE:
<223> OTHER INFORMATION: part of SEQ ID NO. 2

<400> SEQUENCE: 55

Trp Met Thr Gln Thr
1               5

<210> SEQ ID NO 56
<211> LENGTH: 5
```

-continued

```
<212> TYPE: PRT
<213> ORGANISM: artificial
<220> FEATURE:
<223> OTHER INFORMATION: part of SEQ ID NO. 2

<400> SEQUENCE: 56

Pro Gln Leu Trp Leu
1               5

<210> SEQ ID NO 57
<211> LENGTH: 5
<212> TYPE: PRT
<213> ORGANISM: artificial
<220> FEATURE:
<223> OTHER INFORMATION: part of SEQ ID NO. 2

<400> SEQUENCE: 57

Glu Pro Ile Phe Leu
1               5

<210> SEQ ID NO 58
<211> LENGTH: 5
<212> TYPE: PRT
<213> ORGANISM: artificial
<220> FEATURE:
<223> OTHER INFORMATION: part of SEQ ID NO. 2

<400> SEQUENCE: 58

Gln Thr Ala Thr Tyr
1               5

<210> SEQ ID NO 59
<211> LENGTH: 4
<212> TYPE: PRT
<213> ORGANISM: homo sapiens

<400> SEQUENCE: 59

Glu Lys Leu Ser
1

<210> SEQ ID NO 60
<211> LENGTH: 5
<212> TYPE: PRT
<213> ORGANISM: homo sapiens

<400> SEQUENCE: 60

Asp Gly Lys Ala Thr
1               5
```